(12) United States Patent
Andres et al.

(10) Patent No.: US 12,708,426 B2
(45) Date of Patent: Aug. 18, 2026

(54) DEVICES, SYSTEMS AND METHODS FOR SUBDERMAL COAGULATION

(71) Applicant: Apyx Medical Corporation, Clearwater, FL (US)

(72) Inventors: John Andres, Chatham, MA (US); Shawn D Roman, Safety Harbor, FL (US)

(73) Assignee: Apyx Medical Corporation, Clearwater, FL (US)

( * ) Notice: Subject to any disclaimer, the term of this patent is extended or adjusted under 35 U.S.C. 154(b) by 0 days.

(21) Appl. No.: 18/650,342

(22) Filed: Apr. 30, 2024

(65) Prior Publication Data

US 2024/0277397 A1 Aug. 22, 2024

Related U.S. Application Data

(63) Continuation of application No. 16/440,575, filed on Jun. 13, 2019, now abandoned.

(60) Provisional application No. 62/684,830, filed on Jun. 14, 2018.

(51) Int. Cl.

| | |
|---|---|
| ***A61B 18/12*** | (2006.01) |
| ***A61B 18/00*** | (2006.01) |
| ***A61B 18/04*** | (2006.01) |
| ***A61B 18/14*** | (2006.01) |

(52) U.S. Cl.

CPC ........ *A61B 18/1206* (2013.01); *A61B 18/042* (2013.01); *A61B 18/14* (2013.01); *A61B 2018/00178* (2013.01); *A61B 2018/00577* (2013.01); *A61B 2018/00589* (2013.01); *A61B 2018/00601* (2013.01); *A61B 2018/00702* (2013.01); *A61B 2018/1253* (2013.01); *A61B 2018/126* (2013.01)

(58) Field of Classification Search

CPC ........ A61B 18/042; A61B 2018/00452; A61B 2017/00792; A61B 90/02; A61M 2202/08; A61M 1/89

See application file for complete search history.

(56) References Cited

U.S. PATENT DOCUMENTS

| | | | |
|---|---|---|---|
| 1,889,609 | A | 11/1932 | Mutscheller |
| 2,835,254 | A | 5/1958 | Coles |
| 3,299,384 | A | 1/1967 | Lee |
| 3,434,476 | A | 3/1969 | Shaw et al. |
| 3,577,030 | A | 5/1971 | Cusick et al. |
| 3,601,126 | A | 8/1971 | Estes |
| 3,949,266 | A | 4/1976 | Vogts et al. |

(Continued)

FOREIGN PATENT DOCUMENTS

| | | | |
|---|---|---|---|
| CN | 101134203 | A | 3/2008 |
| CN | 103537245 | A | 1/2014 |

(Continued)

*Primary Examiner* — Joseph A Stoklosa
*Assistant Examiner* — Marina Delaney Templeton
(74) *Attorney, Agent, or Firm* — Michael J Porco; Gerald E Hespos

(57) ABSTRACT

Devices, systems and methods are provided for subdermal tissue tightening through soft tissue coagulation and for use in cosmetic surgery applications. The devices, systems and methods of the present disclosure may be used for a minimally invasive application of helium-based cold plasma energy to subcutaneous tissue for the purpose of tightening lax tissue.

17 Claims, 16 Drawing Sheets

(56) References Cited

U.S. PATENT DOCUMENTS 3,952,748 A 4/1976 Kaliher et al.
3,970,088 A 7/1976 Morrison
3,987,795 A 10/1976 Morrison
4,040,426 A 8/1977 Morrison, Jr.
4,041,952 A 8/1977 Morrison, Jr. et al.
4,043,342 A 8/1977 Morrison, Jr.
4,060,088 A 11/1977 Morrison, Jr. et al.
4,255,735 A 3/1981 Liautaud
4,429,694 A 2/1984 McGreevy
4,492,231 A 1/1985 Auth
4,547,721 A 10/1985 Drapp
4,559,943 A 12/1985 Bowers
4,580,551 A 4/1986 Siegmund et al.
4,781,175 A * 11/1988 McGreevy ............ A61B 18/14 219/121.51
4,818,916 A 4/1989 Morrisroe
4,887,005 A 12/1989 Rough et al.
4,890,610 A 1/1990 Kirwan, Sr. et al.
4,897,285 A 1/1990 Wilhelm
4,901,719 A 2/1990 Trenconsky et al.
4,901,720 A 2/1990 Bertrand
4,999,597 A 3/1991 Gaynor
5,088,997 A 2/1992 Delahuerga et al.
5,239,161 A 8/1993 Lang
5,302,881 A 4/1994 O'Loughlin
5,325,019 A 6/1994 Miller et al.
5,452,732 A 9/1995 Bircoll
5,514,153 A 5/1996 Bonutti
5,660,836 A 8/1997 Knowlton
5,669,904 A 9/1997 Platt, Jr. et al.
5,710,486 A 1/1998 Ye et al.
5,717,293 A 2/1998 Sellers
5,720,762 A * 2/1998 Bass ................. A61B 17/0218 606/195
5,725,545 A 3/1998 Bircoll
5,755,753 A 5/1998 Knowlton
5,776,092 A 7/1998 Farin et al.
5,801,489 A 9/1998 Chism, Jr. et al.
5,815,047 A 9/1998 Sorensen et al.
5,871,524 A 2/1999 Knowlton
5,917,286 A 6/1999 Scholl et al.
5,919,219 A 7/1999 Knowlton
5,948,011 A 9/1999 Knowlton
6,039,736 A 3/2000 Platt, Jr.
6,046,546 A 4/2000 Porter et al.
6,099,525 A 8/2000 Cosmescu
6,154,376 A 11/2000 Dan-Harry
6,170,668 B1 1/2001 Babko-Malyi
6,181,068 B1 1/2001 Hur et al.
6,197,026 B1 3/2001 Farin et al.
6,213,999 B1 4/2001 Platt, Jr. et al.
6,222,321 B1 4/2001 Scholl et al.
6,241,753 B1 6/2001 Knowlton
6,262,538 B1 7/2001 Keller
6,311,090 B1 10/2001 Knowlton
6,346,108 B1 2/2002 Fischer
6,348,051 B1 2/2002 Farin et al.
6,350,276 B1 2/2002 Knowlton
6,377,854 B1 4/2002 Knowlton
6,377,855 B1 4/2002 Knowlton
6,381,497 B1 4/2002 Knowlton
6,381,498 B1 4/2002 Knowlton
6,387,380 B1 5/2002 Knowlton
6,405,090 B1 6/2002 Knowlton
6,413,255 B1 7/2002 Stern
6,425,912 B1 7/2002 Knowlton
6,430,446 B1 8/2002 Knowlton
6,438,424 B1 8/2002 Knowlton
6,453,202 B1 9/2002 Knowlton
6,461,378 B1 10/2002 Knowlton
6,470,216 B1 10/2002 Knowlton
6,492,951 B1 12/2002 Harris et al.
6,529,389 B2 3/2003 Perlick et al.
6,616,660 B1 9/2003 Platt
6,627,163 B1 9/2003 Awakowicz et al.
6,749,624 B2 6/2004 Knowlton
6,764,658 B2 7/2004 Denes et al.
6,807,069 B2 10/2004 Nieminen et al.
6,852,112 B2 2/2005 Platt
D506,253 S 6/2005 Cinco
7,006,874 B2 2/2006 Knowlton et al.
7,022,121 B2 4/2006 Stern et al.
7,070,144 B1 7/2006 DiCocco et al.
D527,823 S 9/2006 Levinson
7,115,123 B2 10/2006 Knowlton et al.
7,141,049 B2 11/2006 Stern et al.
7,189,230 B2 3/2007 Knowlton
D544,955 S 6/2007 Carson et al.
7,229,436 B2 6/2007 Stern et al.
7,267,675 B2 9/2007 Stern et al.
7,275,013 B1 9/2007 Matlis et al.
7,316,682 B2 1/2008 Konesky
7,354,435 B2 4/2008 Farin et al.
7,452,358 B2 11/2008 Stern et al.
7,473,251 B2 1/2009 Knowlton et al.
7,481,809 B2 1/2009 Stern et al.
7,537,595 B2 5/2009 McClurken
7,575,597 B2 8/2009 Rehnke
7,615,933 B2 11/2009 Hooke et al.
7,618,429 B2 11/2009 Mulholland
7,630,774 B2 12/2009 Karni et al.
7,744,617 B2 6/2010 Lunsford et al.
7,819,868 B2 10/2010 Cao et al.
7,913,351 B2 3/2011 Moriya
7,927,330 B2 4/2011 Platt
7,928,338 B2 4/2011 Suslov
7,955,330 B2 6/2011 Platt
7,957,815 B2 6/2011 Wyeth et al.
8,057,468 B2 11/2011 Konesky
8,103,355 B2 1/2012 Mulholland
8,121,704 B2 2/2012 Schenck
8,150,532 B2 4/2012 Karni et al.
8,180,458 B2 5/2012 Kane et al.
8,216,218 B2 7/2012 Burns et al.
8,221,410 B2 7/2012 Knowlton et al.
8,267,884 B1 9/2012 Hicks
8,285,392 B2 10/2012 Schenck
8,287,579 B2 10/2012 Nimitz
8,377,388 B2 2/2013 Konesky
8,383,038 B2 2/2013 Kitano
8,394,088 B2 3/2013 West, Jr.
8,409,190 B2 4/2013 Konesky et al.
8,435,194 B2 5/2013 Dverin et al.
8,475,507 B2 7/2013 Dewey et al.
8,506,506 B2 8/2013 Nebrigic et al.
8,515,553 B2 8/2013 Schenck
8,540,745 B2 9/2013 Criscuolo et al.
8,579,835 B2 11/2013 Britva et al.
8,603,088 B2 12/2013 Stern et al.
8,623,012 B2 1/2014 Morgan et al.
8,652,130 B2 2/2014 Kreindel
8,685,017 B2 4/2014 Stern et al.
8,702,691 B2 4/2014 Weber et al.
8,788,060 B2 7/2014 Nebrigic et al.
8,795,265 B2 8/2014 Konesky et al.
8,802,022 B2 8/2014 Konesky
8,882,758 B2 11/2014 Nebrigic et al.
8,906,009 B2 12/2014 Nebrigic et al.
8,950,406 B2 2/2015 Karni et al.
9,060,765 B2 6/2015 Rencher et al.
9,119,284 B2 8/2015 Sanematsu
9,144,453 B2 9/2015 Rencher et al.
9,161,802 B2 10/2015 Przybyszewski
9,168,096 B2 10/2015 Kreindel
9,215,788 B2 12/2015 Karni et al.
9,277,953 B2 3/2016 Williams et al.
9,283,029 B2 3/2016 Britva et al.
9,326,809 B2 5/2016 Williams et al.
9,333,258 B2 5/2016 Almutairi et al.
9,333,259 B2 5/2016 Almutairi et al.
9,522,289 B2 12/2016 Almutairi et al.
9,545,284 B2 1/2017 Karni
9,545,529 B2 1/2017 Britva et al.
9,603,653 B2 3/2017 Schnitzler et al.

(56) References Cited

U.S. PATENT DOCUMENTS 9,636,175 B2 5/2017 Stern et al.
9,649,143 B2 5/2017 Konesky et al.
10,188,461 B2 1/2019 Almutairi et al.
10,918,433 B2 2/2021 Konesky et al.
11,129,665 B2 9/2021 Konesky
2001/0020167 A1 9/2001 Woloszko et al.
2002/0095151 A1 7/2002 Dahla et al.
2002/0156471 A1 10/2002 Stern et al.
2003/0105458 A1 6/2003 Platt
2003/0130653 A1 7/2003 Sixto, Jr. et al.
2003/0212393 A1 11/2003 Knowlton et al.
2004/0000316 A1 1/2004 Knowlton et al.
2004/0034342 A1 2/2004 Barton et al.
2004/0044342 A1 3/2004 Mackay
2004/0116918 A1 6/2004 Konesky
2004/0206365 A1* 10/2004 Knowlton .............. A61B 18/14 128/898
2005/0015086 A1 1/2005 Platt
2005/0118350 A1 6/2005 Koulik et al.
2005/0187542 A1 8/2005 Auge et al.
2005/0234442 A1 10/2005 Spears
2005/0240147 A1 10/2005 Makower et al.
2005/0245961 A1 11/2005 Mollenauer et al.
2006/0005545 A1 1/2006 Samimy et al.
2006/0206110 A1 9/2006 Knowlton et al.
2006/0224154 A1 10/2006 Shadduck et al.
2007/0010811 A1 1/2007 Stern et al.
2007/0032747 A1 2/2007 Hashimshony et al.
2007/0078502 A1 4/2007 Weber et al.
2007/0089795 A1 4/2007 Jacob
2007/0265614 A1 11/2007 Stern et al.
2008/0058783 A1 3/2008 Altshuler et al.
2008/0076958 A1 3/2008 Britva et al.
2008/0108985 A1 5/2008 Konesky
2008/0193329 A1 8/2008 Akishev et al.
2008/0200969 A1 8/2008 Weber
2008/0262488 A1 10/2008 Penny et al.
2008/0287943 A1 11/2008 Weber et al.
2008/0302767 A1 12/2008 Yamaguchi et al.
2009/0012585 A1 1/2009 Karni et al.
2009/0024122 A1 1/2009 Fischer
2009/0076732 A1 3/2009 Sprigle et al.
2009/0149930 A1 6/2009 Schenck
2009/0171339 A1 7/2009 Young et al.
2009/0171424 A1 7/2009 Britva et al.
2009/0270849 A1 10/2009 Truckai et al.
2009/0281537 A1 11/2009 Britva et al.
2009/0318909 A1 12/2009 DeBenedictis et al.
2009/0326571 A1 12/2009 Mulholland
2010/0010480 A1 1/2010 Mehta et al.
2010/0021340 A1 1/2010 Buske et al.
2010/0023003 A1 1/2010 Mulholland
2010/0100094 A1* 4/2010 Truckai ................ A61B 18/042 606/39
2010/0256530 A1 10/2010 Varghese et al.
2010/0286684 A1 11/2010 Hata et al.
2011/0015621 A1 1/2011 Kreindel
2011/0071517 A1 3/2011 Konesky et al.
2011/0077585 A1 3/2011 Canady
2011/0112520 A1 5/2011 Michael
2011/0130683 A1 6/2011 Sarvazyan
2011/0202048 A1 8/2011 Nebrigic
2011/0202084 A1 8/2011 Hoem et al.
2011/0301412 A1 12/2011 Cho
2012/0041434 A1 2/2012 Truckai
2012/0065635 A1 3/2012 Konesky
2012/0071794 A1 3/2012 Karni
2012/0092739 A1 4/2012 Frangineas
2012/0109264 A1 5/2012 Frangineas
2012/0116397 A1 5/2012 Rencher et al.
2012/0172789 A1 7/2012 Fischer et al.
2012/0215134 A1 8/2012 Hunter-Jones et al.
2012/0239120 A1 9/2012 Karni et al.
2012/0245580 A1 9/2012 Germain et al.
2012/0283725 A1 11/2012 Knowlton et al.
2012/0325704 A1 12/2012 Kerns et al.
2013/0060309 A1 3/2013 Bradley
2013/0090643 A1 4/2013 Williams et al.
2013/0090644 A1 4/2013 Williams et al.
2013/0103410 A1 4/2013 Carnell et al.
2013/0237982 A1 9/2013 Rencher et al.
2013/0274742 A1* 10/2013 Schnitzler ............ A61B 18/042 606/49
2013/0291658 A1 11/2013 Pailler-Mattei et al.
2013/0310817 A1 11/2013 Frangineas
2014/0005644 A1 1/2014 Karni et al.
2014/0005665 A1 1/2014 Konesky et al.
2014/0007895 A1 1/2014 Britva et al.
2014/0121569 A1 5/2014 Schafer et al.
2014/0128944 A1 5/2014 Stern et al.
2014/0142469 A1 5/2014 Britva et al.
2014/0236049 A1 8/2014 Barthe et al.
2014/0316403 A1 10/2014 Konesky et al.
2014/0336733 A1 11/2014 Nebrigic et al.
2014/0341786 A1 11/2014 Konesky
2014/0358068 A1* 12/2014 Almutairi .............. A61N 5/062 604/20
2015/0025418 A1 1/2015 Shih et al.
2015/0045857 A1 2/2015 Britva et al.
2015/0080991 A1 3/2015 Britva et al.
2015/0132711 A1 5/2015 Mason
2015/0182763 A1 7/2015 Slayton et al.
2015/0257817 A1 9/2015 Zoran et al.
2015/0297908 A1 10/2015 Alinsod et al.
2015/0305795 A1 10/2015 Varney et al.
2015/0374275 A1 12/2015 Peipsi et al.
2016/0157916 A1 6/2016 Germain et al.
2016/0263387 A1 9/2016 Alinsod et al.
2016/0263388 A1 9/2016 Alinsod et al.
2016/0263389 A1 9/2016 Alinsod et al.
2016/0287310 A1 10/2016 Nettesheim et al.
2016/0310006 A1 10/2016 Aguero Villarreal et al.
2017/0049494 A1 2/2017 Stern et al.
2017/0049496 A1 2/2017 Konesky et al.
2017/0135715 A1 5/2017 Breindel et al.
2017/0245909 A1 8/2017 Konesky et al.
2018/0014777 A1 1/2018 Amir et al.
2018/0085155 A1 3/2018 Konesky et al.
2018/0103991 A1* 4/2018 Linhart .............. A61B 18/1477
2018/0236254 A1 8/2018 Schwarz et al.
2019/0254734 A1 8/2019 Konesky
2019/0380766 A1 12/2019 Andres et al.
2019/0388135 A1 12/2019 Gogolin et al.
2020/0060749 A1 2/2020 Shilev et al.
2022/0249150 A1 8/2022 Roman et al.

FOREIGN PATENT DOCUMENTS

CN 103537245 B 11/2015
DE 102013113941 A1 6/2015
EP 0765638 A1 4/1997
JP 2004108794 A 4/2004
JP 3726794 B2 12/2005
JP 2007305845 A 11/2007
JP 2008053661 A 3/2008
WO 9116003 A1 10/1991
WO 9926546 A1 6/1999
WO 03105689 A1 12/2003
WO 2006100030 A1 9/2006
WO 2007071720 A1 6/2007
WO 2011029573 A1 3/2011
WO 2015059702 A1 4/2015
WO 2015087287 A1 6/2015
WO 2019121592 A1 6/2019

* cited by examiner 620
619D
619C
618
619A 621A
619B
Top View
620
621B
621B
620
618
621A
621A
618
(Right)
(Left)
624
623D
622
623A
623C 625A
623B
Top View
625B
624
622
625A
626
627B
627A

628

632
630
631A

Top View
632
631B
630
631A
(Left)
632
631B
631A
630
(Right)
636
634
635A

Top View
636
635B
(Right)
634
635A
635B
(Left)
634
636
635A
638
639A

640
Top View
639B
(Right)
639A
638
639B
638
(Left)
639A

DEVICES, SYSTEMS AND METHODS FOR SUBDERMAL COAGULATION

PRIORITY

This application is a continuation application of U.S. patent application Ser. No. 16/440,575, filed Jun. 13, 2019, which claims priority to U.S. Provisional Patent Appl. No. 62/684,830, filed Jun. 14, 2018, entitled "DEVICES, SYSTEMS AND METHODS FOR SUBDERMAL COAGULATION, the contents of which are hereby incorporated by reference in its entirety.

BACKGROUND

Field

The present disclosure relates generally to electrosurgery and electrosurgical systems and apparatuses, and more particularly, to electrosurgical devices, systems and methods for subdermal tissue tightening through soft tissue coagulation and for use in cosmetic surgery applications.

Description of the Related Art

High frequency electrical energy has been widely used in surgery and is commonly referred to as electrosurgical energy. Tissue is cut and bodily fluids are coagulated using electrosurgical energy.

Gas plasma is an ionized gas capable of conducting electrical energy. Plasmas are used in surgical devices to conduct electrosurgical energy to a patient. The plasma conducts the energy by providing a pathway of relatively low electrical resistance. The electrosurgical energy will follow through the plasma to cut, coagulate, desiccate, or fulgurate blood or tissue of the patient. There is no physical contact required between an electrode and the tissue treated.

Electrosurgical systems that do not incorporate a source of regulated gas can ionize the ambient air between the active electrode and the patient. The plasma that is thereby created will conduct the electrosurgical energy to the patient, although the plasma arc will typically appear more spatially dispersed compared with systems that have a regulated flow of ionizable gas.

Atmospheric pressure discharge cold plasma applicators have found use in a variety of applications including surface sterilization, hemostasis, and ablation of tumors. Often, a simple surgical knife is used to excise the tissue in question, followed by the use of a cold plasma applicator for cauterization, sterilization, and hemostasis. Cold plasma beam applicators have been developed for both open and endoscopic procedures. In the latter case, it is often desirable to be able to redirect the position of the cold plasma beam tip to a specific operative site. The external incision and pathway for the endoscopic tool may be chosen to avoid major blood vessels and non-target organs and may not coincide with an optimum alignment for the target internal tissue site. A means of redirecting the cold plasma beam is essential in these situations.

Thermal-induced contraction of collagen through the coagulation of soft tissue is well known in medicine and is used in ophthalmology, orthopedic applications, and the treatment of varicose veins. The reported range of temperatures causing collagen contraction varies from 60° C. to 80° C. Therefore, once tissue is heated to within this range, protein denaturation and collagen contraction occur resulting in the reduction in volume and surface area of the heated tissue. Noninvasive use of radiofrequency devices, lasers, and plasma devices have been used for the reduction of facial wrinkles and rhytides caused by thermal-induced collagen/tissue contraction since the mid-1990s.

SUMMARY

The present disclosure relates to devices, systems and methods for subdermal tissue tightening through soft tissue coagulation and for use in cosmetic surgery applications. The devices, systems and methods of the present disclosure may be used for a minimally invasive application of plasma energy to subcutaneous tissue for the purpose of tightening lax tissue.

In one aspect of the present disclosure, a surgical method is provided including creating an entry incision through the epidermal and dermal layers of a patient's skin; disposing a balloon device in a subcutaneous layer through the entry incision; inflating the balloon to dissect tissue to create a dissected tissue plane; and applying helium-based cold plasma in the dissected tissue plane to coagulate tissue and reduce laxity in the patient's skin.

In another aspect, the applying the helium-based cold plasma includes: flowing helium over an energized electrode and ionizing a portion of the flowing helium to generate the cold plasma for coagulating the tissue, wherein an un-ionized portion of the flowing helium removes heat from the coagulated tissue.

In another aspect, the ionized portion is approximately less than 0.1% of the volume of the flowing helium and the un-ionized portion is approximately greater than 99.9% of the volume of the flowing helium.

In another aspect, the balloon device is disposed in a subcutaneous layer by a tunneling member.

In another aspect, the balloon device is disposed in a subcutaneous layer by a cold plasma generator.

In another aspect, the balloon is inflated with helium supplied by the cold plasma generator.

In another aspect, the helium-based cold plasma is applied in a wanding motion to optimize distribution of the plasma.

In another aspect, the method further includes deflating the balloon device and removing the balloon device before the applying of the helium-based cold plasma.

In another aspect, the method includes wherein the balloon device remains inflated during the applying of the helium-based cold plasma to promote flow of the plasma to extremities of the dissected tissue plane.

In another aspect, the balloon device is configured to correspond to an area of skin of a patient to be tightened.

In another aspect, the balloon device is configured to correspond to at least one of a patient's buttocks, abdomen, arms, legs, neck, forehead and/or chin.

In another aspect, the method includes wherein the helium-based cold plasma finds tissue that represents the path of least resistance for flow of RF energy in a plasma beam, and further comprises drawing the helium-based cold plasma through the dissected tissue plane such that the path of least resistance constantly changes to effect 360 degree tissue treatment.

In another aspect, the path of least resistance is individual bands of a fibroseptal network in the dissected tissue plane.

In another aspect, the path of least resistance is tissue having a lowest impedance relative to adjacent tissue.

In another aspect, the helium-based cold plasma is applied at a constant power output level for a range of tissue impedances.

In another aspect, the helium-based cold plasma is applied at a power output level of about 40 watts for tissue impedances on a range of about 125 ohms to at least about 5000 ohms.

In another aspect, a system is provided including an electrosurgical generator coupled to a power source and configured for generating electrosurgical energy; a plasma generator including a gas conduit and an electrode disposed within the gas conduit, the electrode operatively coupled to the electrosurgical generator to selectively receive electrosurgical energy therefrom such that the electrode at least partially ionizes a helium supplied to the gas conduit to create a plasma discharge; and a balloon device configured to be disposed in tissue and to dissect tissue when inflated to create a dissected tissue plane, wherein the plasma generator coagulates tissue by applying the plasma discharge in the dissected tissue plane.

In another aspect, an electrosurgical handpiece is provided including a plasma generator including a gas conduit and an electrode disposed within the gas conduit, the electrode operatively coupled to an electrosurgical generator to selectively receive electrosurgical energy therefrom such that the electrode at least partially ionizes a helium supplied to the gas conduit to create a plasma discharge at the distal end of the gas conduit; and a balloon device coupled to the gas conduit and configured to be disposed in tissue and to dissect tissue when inflated to create a dissected tissue plane, wherein the plasma generator coagulates tissue by applying the plasma discharge in the dissected tissue plane.

In another aspect, a surgical kit is provided including a sterile enclosure; a plasma generator disposed in the sterile enclosure, the plasma generator including a gas conduit and an electrode disposed within the gas conduit, the electrode configured to be coupled to an electrosurgical generator to selectively receive electrosurgical energy therefrom such that the electrode at least partially ionizes a helium supplied to the gas conduit to create a plasma discharge at the distal end of the gas conduit; and at least one balloon device disposed in the sterile enclosure, the at least one balloon device configured to be disposed in tissue and to dissect tissue when inflated to create a dissected tissue plane, wherein the plasma generator coagulates tissue by applying the plasma discharge in the dissected tissue plane.

BRIEF DESCRIPTION OF THE DRAWINGS

The above and other aspects, features, and advantages of the present disclosure will become more apparent in light of the following detailed description when taken in conjunction with the accompanying drawings in which.

Figure 1:
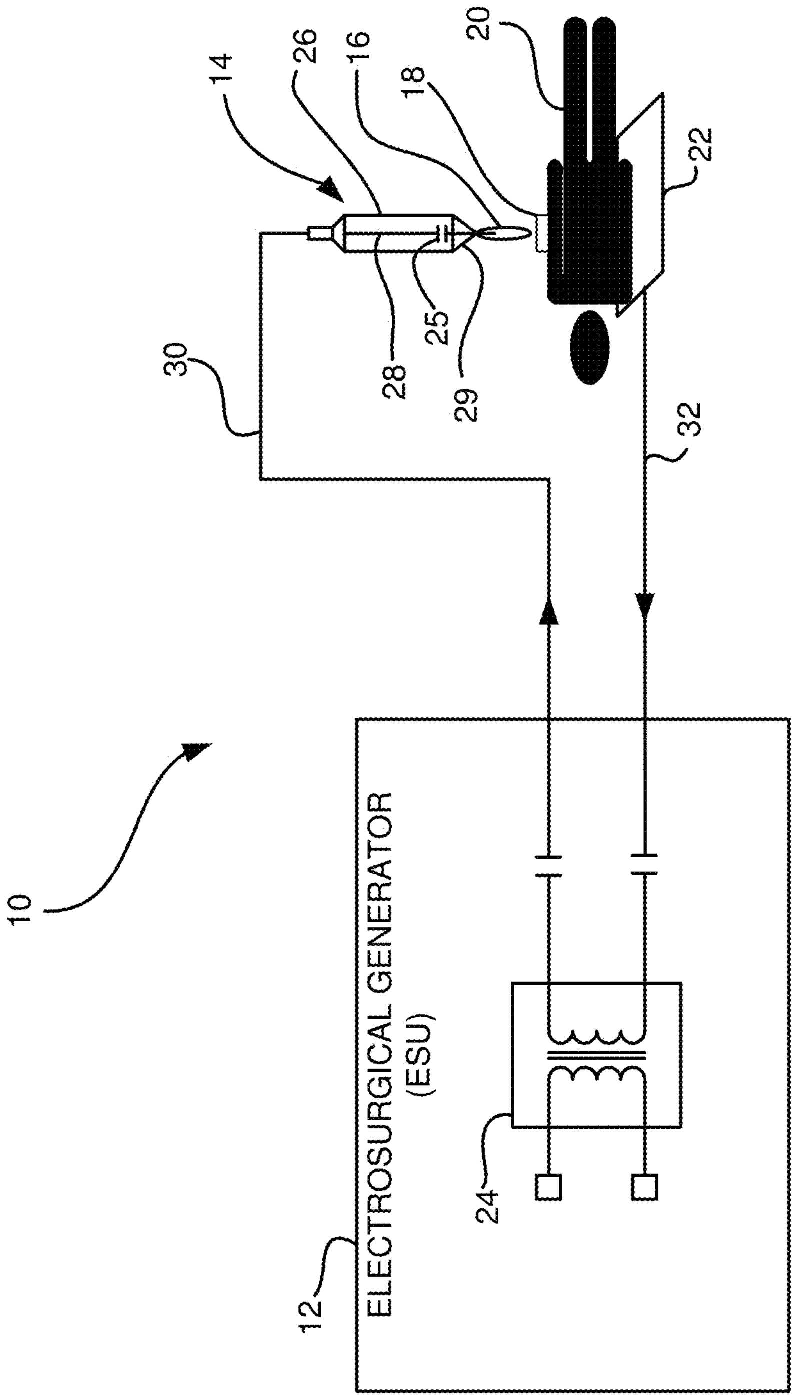
FIG. 1 is an illustration of an exemplary electrosurgical system in accordance with an embodiment of the present disclosure.

It should be understood that the drawings are for purposes of illustrating the concepts of the disclosure and are not necessarily the only possible configuration for illustrating the disclosure.

DETAILED DESCRIPTION

Preferred embodiments of the present disclosure will be described hereinbelow with reference to the accompanying drawings. In the following description, well-known functions or constructions are not described in detail to avoid obscuring the present disclosure in unnecessary detail. In the drawings and in the description which follow, the term "proximal", as is traditional, will refer to the end of the device, e.g., instrument, apparatus, applicator, handpiece, forceps, etc., which is closer to the user, while the term "distal" will refer to the end which is further from the user. Herein, the phrase "coupled" is defined to mean directly connected to or indirectly connected with through one or more intermediate components. Such intermediate components may include both hardware and software based components.

Recently, the use of thermal-induced collagen/tissue contraction has been expanded to minimally invasive procedures. Laser-assisted lipolysis (LAL) and radiofrequency-assisted lipolysis (RFAL) devices have combined the removal of subcutaneous fat with soft tissue heating to reduce the skin laxity that often results from fat volume removal. These devices are placed in the same subcutaneous tissue plane as a standard suction-assisted lipolysis (SAL) cannula and are used to deliver thermal energy to coagulate the subcutaneous tissue including the underside of the dermis, the fascia, and the septal connective tissue. The coagulation of the subcutaneous tissue results in collagen/tissue contraction that reduces skin laxity.

The devices, systems and methods of the present disclosure are employed for the minimally invasive application of helium-based cold plasma energy to subcutaneous tissue for the purpose of tightening lax tissue. A tip of a plasma generating handpiece is placed in the subcutaneous tissue plane through the same access ports used for SAL. Activation of the plasma generating handpiece in this plane causes contraction of the collagen contained in the dermis, the fascia, and the septal connective matrix through precise heating from the plasma energy.

FIG. 1 shows an exemplary electrosurgical system generally indicated as 10 comprising an electrosurgical generator (ESU) generally indicated as 12 to generate power for the electrosurgical apparatus 10 and a plasma generator generally indicated as 14 to generate and apply a plasma stream 16 to a surgical site or target area 18 on a patient 20 resting on a conductive plate or support surface 22. The electrosurgical generator 12 includes a transformer generally indicated as 24 including a primary and secondary coupled to an electrical source (not shown) to provide high frequency electrical energy to the plasma generator 14. Typically, the electrosurgical generator 12 comprises an isolated floating potential not referenced to any potential. Thus, current flows between the active and return electrodes. If the output is not isolated, but referenced to "earth", current can flow to areas with ground potential. If the contact surface of these areas and the patient is relatively small, an undesirable burning can occur.

The plasma generator 14 comprises a handpiece or holder 26 having an electrode 28 at least partially disposed within a fluid flow housing 29 and coupled to the transformer 24 to receive the high frequency electrical energy therefrom to at least partially ionize noble gas fed to the fluid flow housing 29 of the handpiece or holder 26 to generate or create the plasma stream 16. The high frequency electrical energy is fed from the secondary of the transformer 24 through an active conductor 30 to the electrode 28 (collectively active electrode) in the handpiece 26 to create the plasma stream 16 for application to the surgical site 18 on the patient 20. Furthermore, a current limiting capacitor 25 is provided in series with the electrode 28 to limit the amount of current being delivered to the patient 20.

The return path to the electrosurgical generator 12 is through the tissue and body fluid of the patient 20, the conductor plate or support member 22 and a return conductor 32 (collectively return electrode) to the secondary of the transformer 24 to complete the isolated, floating potential circuit.

In another embodiment, the electrosurgical generator 12 comprises an isolated non-floating potential not referenced to any potential. The plasma current flow back to the electrosurgical generator 12 is through the tissue and body fluid and the patient 20. From there, the return current circuit is completed through the combined external capacitance to the plasma generator handpiece 26, surgeon and through displacement current. The capacitance is determined, among other things, by the physical size of the patient 20. Such an electrosurgical apparatus and generator are described in commonly owned U.S. Pat. No. 7,316,682 to Konesky, the contents of which are hereby incorporated by reference in its entirety.

It is to be appreciated that transformer 24 may be disposed in the plasma generator handpiece 26, as will be described in various embodiments below. In this configuration, other transformers may be provided in the generator 12 for providing a proper voltage and current to the transformer in the handpiece 26, e.g., a step-down transformer, a step-up transformer or any combination thereof. Alternatively, the transformer may be located in the generator.

Figures 2A, 2B:
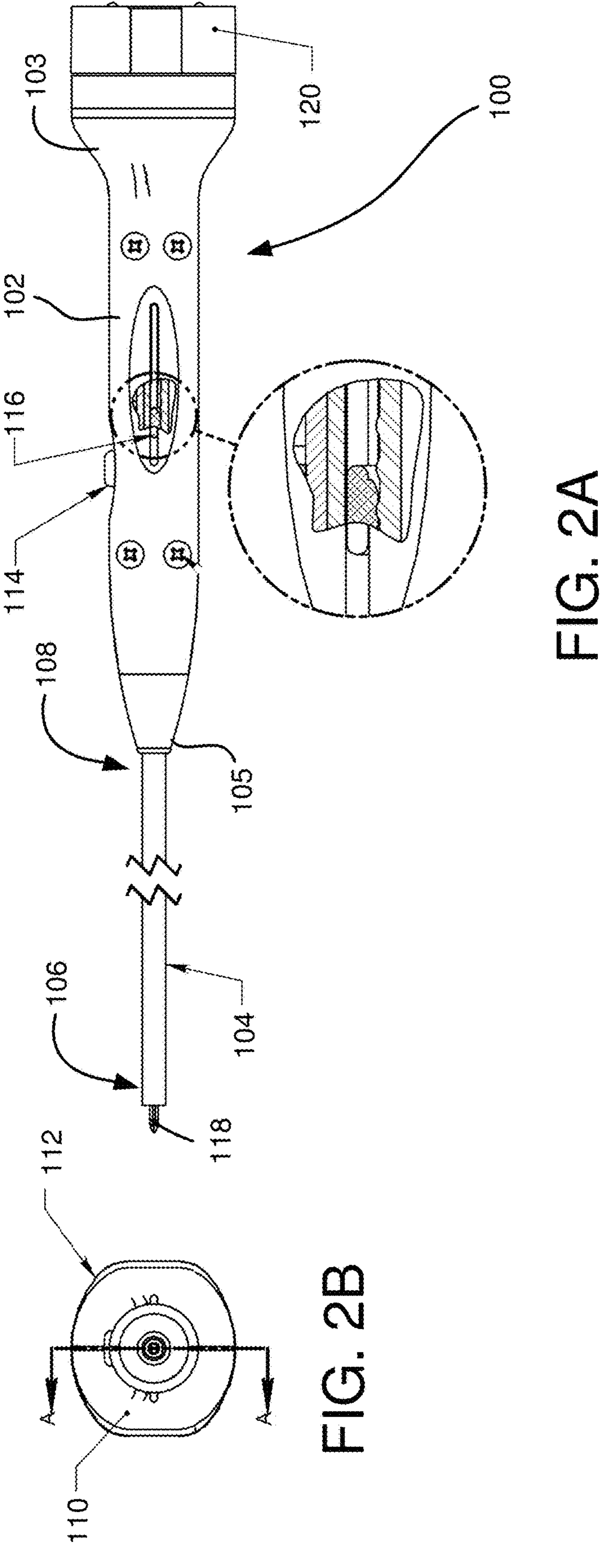
FIG. 2A is a schematic diagram showing a side view of an electrosurgical apparatus in accordance with an embodiment of the present disclosure.
FIG. 2B is a front view of the electrosurgical apparatus shown in FIG. 2A.
Figure 2C:
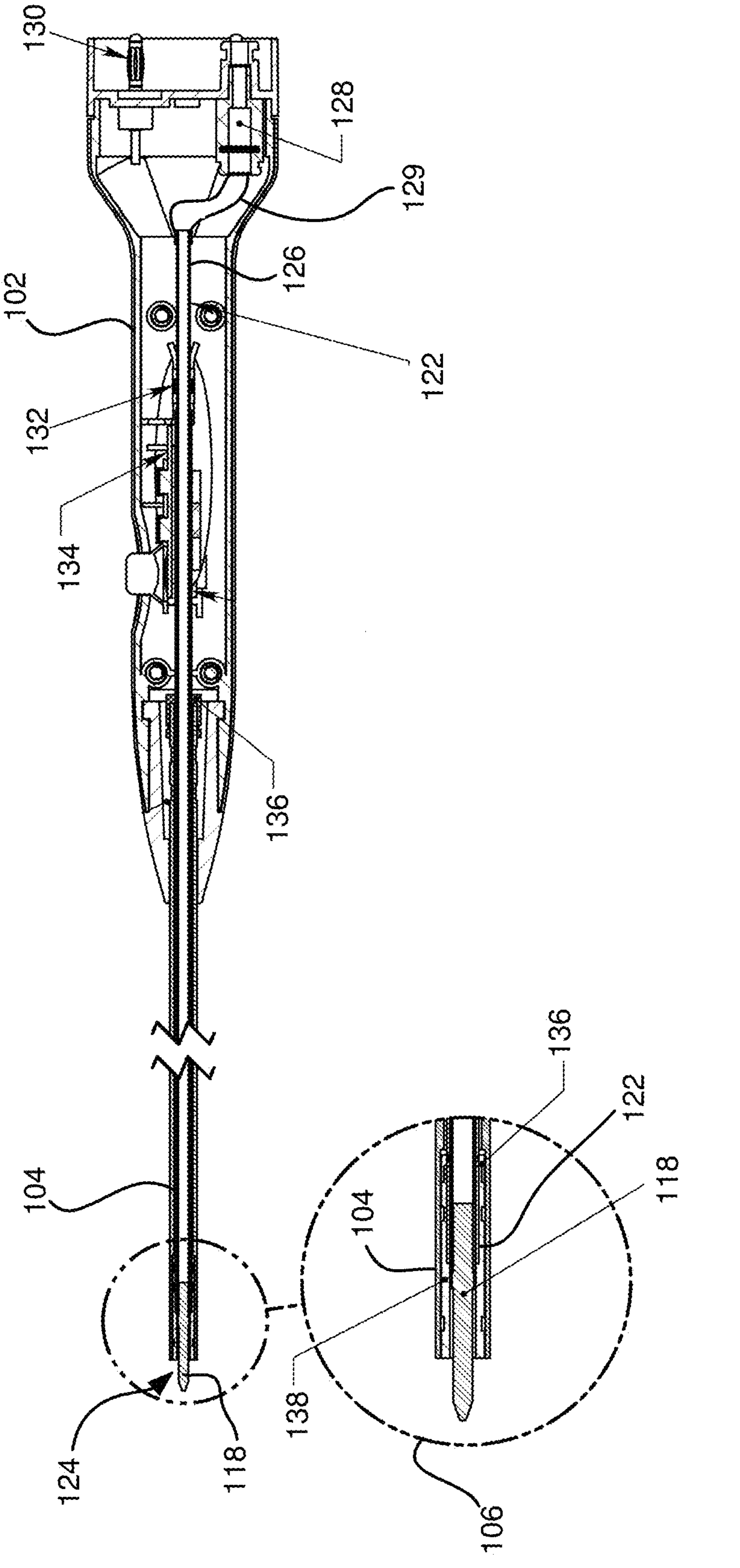
FIG. 2C is a cross sectional view of the electrosurgical apparatus shown in FIG. 2A taken along line A-A.

Referring to FIGS. 2A-2C, an electrosurgical handpiece or plasma generator 100 in accordance with the present disclosure is illustrated. Generally, the handpiece 100 includes a housing 102 having a proximal end 103 and a distal end 105 and a tube 104 having an open distal end 106 and a proximal end 108 coupled to the distal end 105 of the housing 102. The housing 102 includes a right side housing 110 and left side housing 112, and further includes provisions for a button 114 and slider 116. Activation of the slider 116 will expose an optional blade 118 at the open distal end 106 of the tube 104. Activation of the button 114 will apply electrosurgical energy to the blade 118 and, in certain embodiments, enable gas flow through the flow tube 122, as will be described in detail below.

Additionally, a transformer 120 may be provided on the proximal end 103 of the housing 102 for coupling a source of radio frequency (RF) energy to the handpiece 100. By providing the transformer 120 in the handpiece 100 (as opposed to locating the transformer in the electrosurgical generator), power for the handpiece 100 develops from higher voltage and lower current than that required when the transformer is located remotely in the generator, which results in lower thermalization effects. In contrast, a transformer back in the generator produces applicator power at a lower voltage, higher current with greater thermalization effects. Therefore, by providing the transformer 120 in handpiece 100, collateral damage to tissue at the operative site is minimized. While providing the transformer in the handle has advantages, it is contemplated that the transformer may be disposed in the generator.

A cross section view along line A-A of the housing 102 is shown in FIG. 2C. Disposed within the housing 102 and tube 104 is flow tube 122 which runs along the longitudinal axis of the handpiece or plasma generator 100. On a distal end 124 of the flow tube 122, the blade 118 is retained within the flow tube 122. A proximal end 126 of the flow tube 122 is coupled to a source of gas via a tube connector 128 and flexible tubing 129. The proximal end 126 of the flow tube 122 is also coupled to a source of RF energy via plug 130 which couples to transformer 120. The flow tube 122 is made of an electrically conducting material, preferably stainless steel, as to conduct the RF energy to the blade 118 when being employed for plasma applications or electrosurgical cutting as will be described below. The outer tube 104 is constructed from non-conductive material, e.g., Lestran™. The slider 116 is coupled to the flow tube 122 via a retaining collar 132. A printed circuit board (PCB) 134 is disposed in the housing 102 and controls the application of the RF energy from the transformer 120 via the button 114.

It is to be appreciated that the slider 116 may be freely moveable in a linear direction or may include a mechanism for incremental movements, e.g., a ratchet movement, to prevent an operator of the handpiece 100 from over extending the blade 118. By employing a mechanism for incremental movements of the optional blade 118, the operator will have greater control over the length of the exposed blade 118 to avoid damage to tissue at the surgical site. It is also contemplated that the slider may extend a needle or blunt probe instead of a blade, with extension or retraction of the blade/needle/probe helping to control the characteristics of the energy transfer to the gas and, in combination with gas flow, the beam shape and intensity.

An enlarged view of the distal end 106 of the outer tube 104 is also illustrated in FIG. 2C. Here, the blade 118 is coupled to the flow tube 122 which is held in place in the outer tube 104 by at least one seal 136. The at least one seal 136 prevents backflow of gas into tube 104 and housing 102. A cylindrical ceramic insert 138 is disposed in the distal end of the outer tube 104 to maintain the blade along the longitudinal axis of the handpiece 100 and provide structural support during mechanical cutting when the blade is exposed beyond the distal end of the outer tube 104.

Figures 3A, 3B:
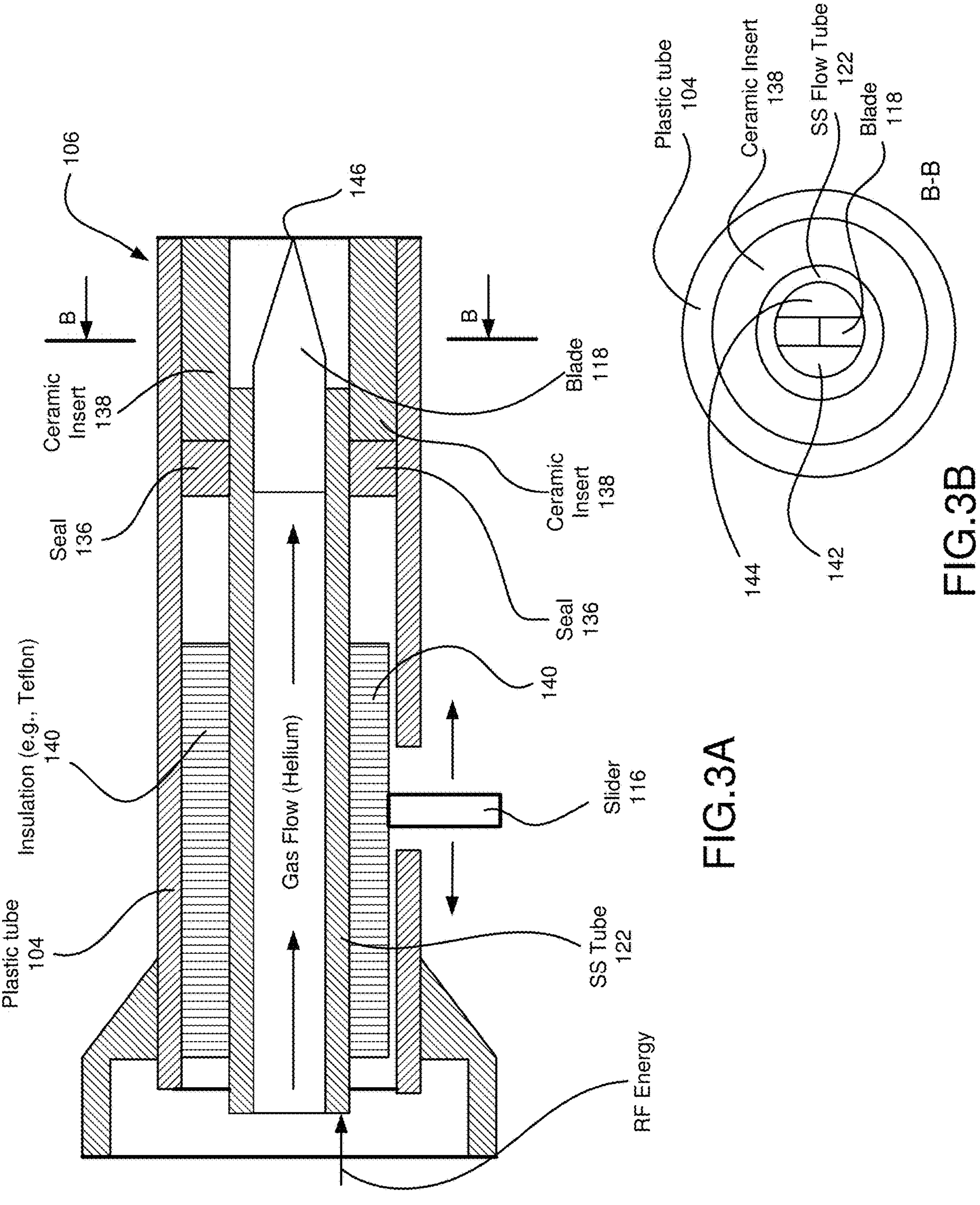
FIG. 3A is an enlarged cross-sectional view of the electrosurgical apparatus in accordance with an embodiment of the present disclosure.
FIG. 3B illustrates a front view of the electrosurgical apparatus shown in FIG. 3A taken along line B-B.

The operational aspect of the handpiece 100 will now be described in relation to FIGS. 3A and 3B, where FIG. 3A shows an enlarged cross section of the apparatus and FIG. 3B illustrates a front view of the apparatus.

Referring to FIG. 3A, the flow tube 122 is disposed in the outer tube 104 with a cylindrical insulator 140 disposed around the flow tube 122. Slider 116 is coupled to the insulator 140 and is employed to extend and retract the blade 118. At the distal end 106 of the outer tube 104, the annular or ring-shaped seal 136 and cylindrical ceramic insert 138 are disposed about the flow tube 122. As can be seen In FIG. 3B, the generally planar blade 118 is coupled to an inner circumference of the cylindrical flow tube 122 such that two gas passageways 142, 144 are formed on the both sides of the blade 118. As gas flows from the proximal end 103 of the housing through the flow tube 122, the gas will pass over the blade 118 out the distal end of the outer tube 104.

Figure 11:
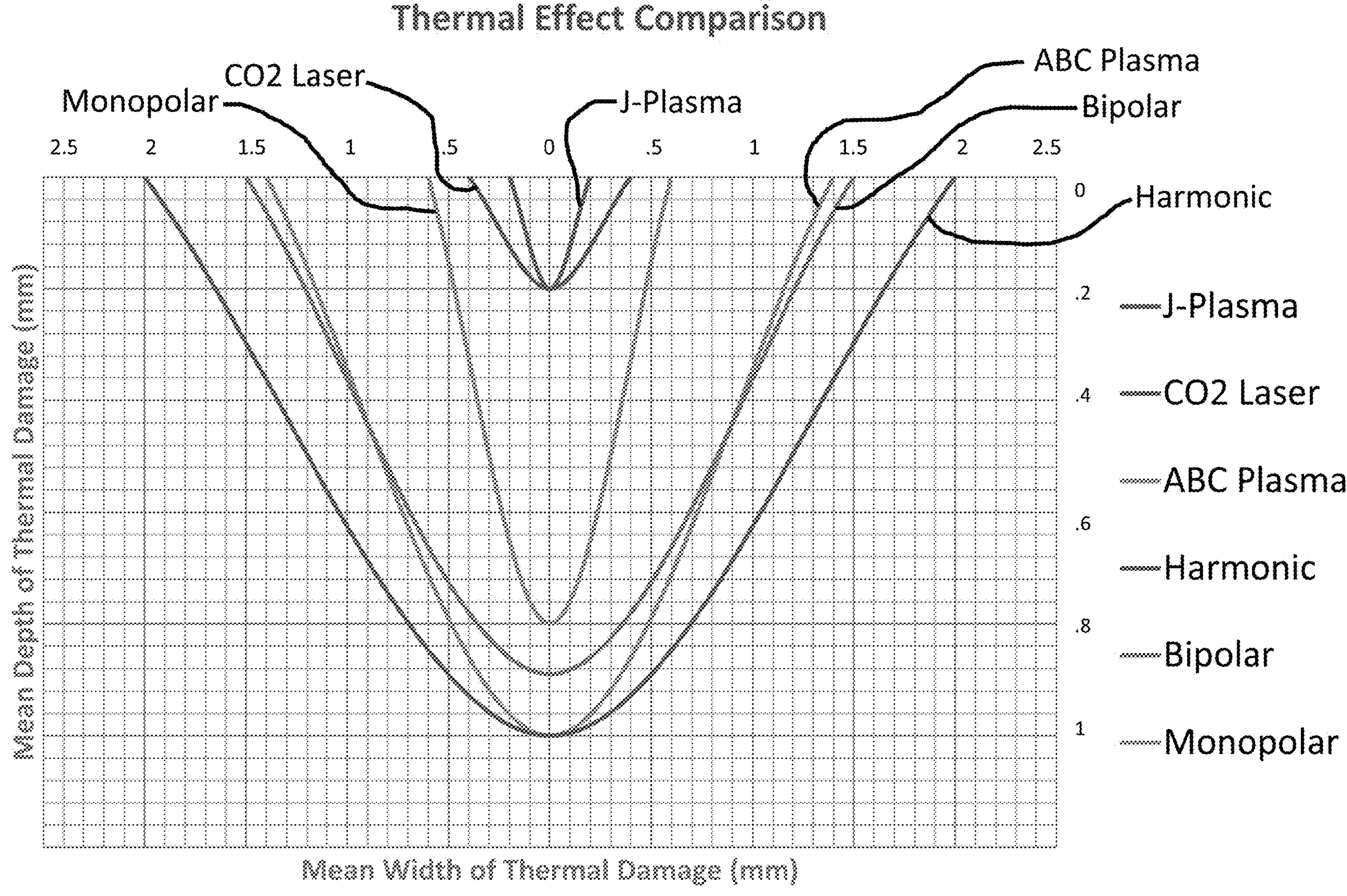
FIG. 11. is a graph comparing the thermal effects on tissue caused by various devices.

When the blade is in the retracted position as shown in FIG. 3A, the apparatus 102 is suitable for generating plasma. In the retracted position, RF energy is conducted to a tip 146 of the blade 118 from an electrosurgical generator (not shown) via the flow tube 122. An inert gas, such as helium, is then supplied through the flow tube 122 from either the electrosurgical generator or an external gas source. As the inert gas flows over the sharp point 146 of the blade 118 held at high voltage and high frequency, a cold plasma beam is generated. While other inert gases are known and are used in generating plasma for surgical applications, e.g. argon, helium is preferred due to its simple molecular structure which translates into the following advantages: (i) Helium can be ionized with low input of energy; (ii) With only two electrons compared to eighteen for argon, the ionization of helium is more controlled, which produces a more stable and less aggressive plasma beam; and (iii) Helium has high thermal conductivity (10 times higher than argon). In a cold plasma, less than 0.1% of the gas is ionized. Therefore, in a cold helium plasma, more than 99.9% of the highly thermally conductive un-ionized helium is available as a heat sink to remove heat from the application site. These three advantages of helium allow for precise, immediate heating and contraction of the target tissue followed by immediate cooling with minimal depth of thermal effect. Referring to FIG. 11, the depth and width of thermal damage to tissue is illustrated for various devices, for example, a helium-based cold plasma (J-Plasma) device, a CO2 laser device, an ABC (Argon Beam Coagulation) device, a harmonic device, a bipolar electrosurgical device and a monopolar electrosurgical device. As shown in FIG. 11, among the compared devices, a helium-based cold plasma device in accordance with the present disclosure results in minimal depth and width of thermal damage. The cold plasma generated with helium is ideal for the applications of subdermal skin tightening, coagulation, sculpting and contouring as contemplated herein.

Figure 4:
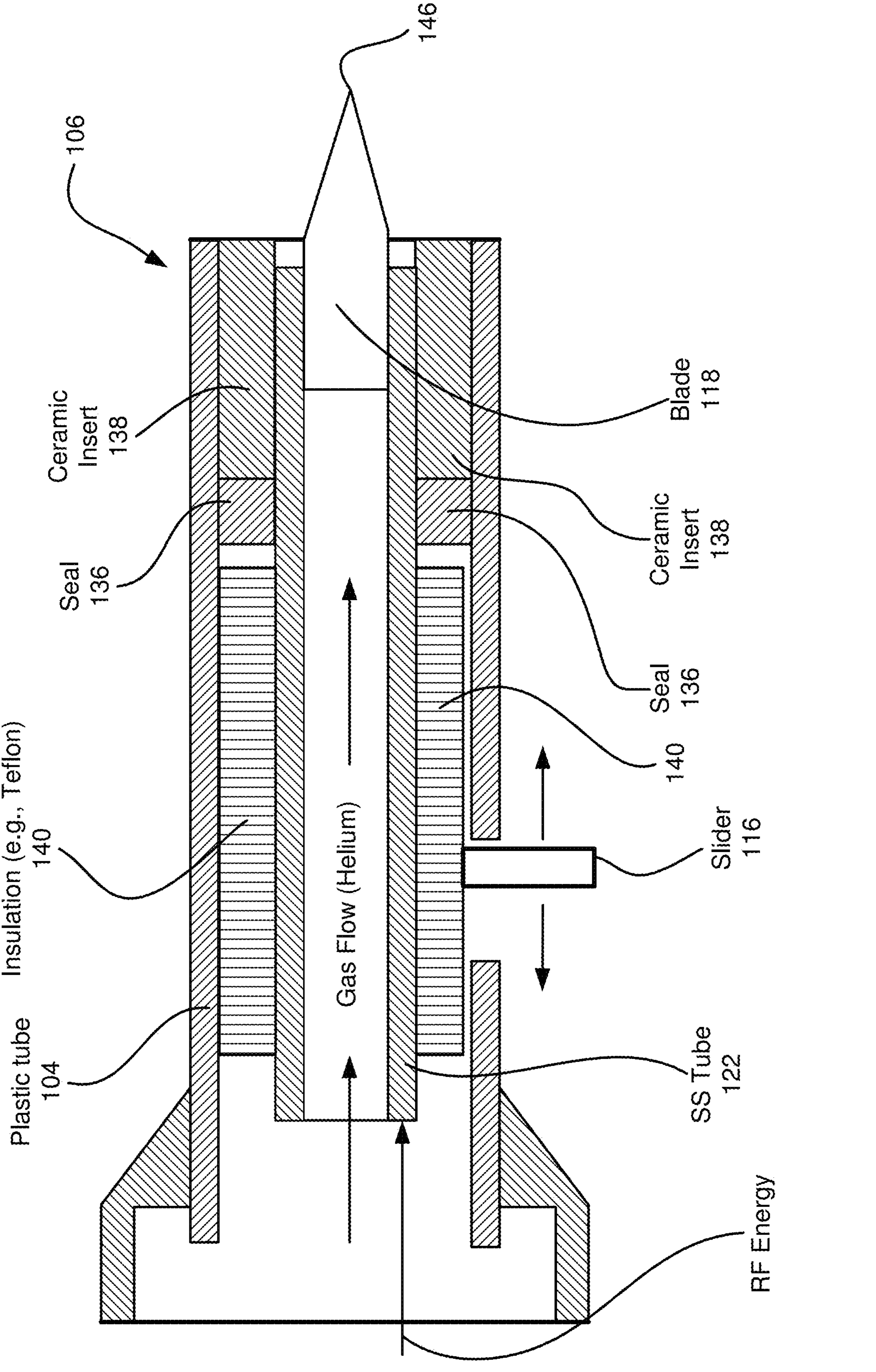
FIG. 4 is an enlarged cross-sectional view of the electrosurgical apparatus shown in FIG. 3A with a blade extended.

Referring to FIG. 4, the blade 118 is advanced, via slider 116, so the tip 146 is extended past the distal end 106 of the outer tube 104. In this state, the blade 118 can be used for two cutting modes: mechanical cutting and electrosurgical cutting. In the mechanical cutting mode, RF or electrosurgical energy is not applied to the flow tube 122 or blade 118, and therefore, the blade 118 is in a de-energized state. In this mode, the blade 118 can be used to excise tissue via mechanical cutting, i.e., using the blade to make contact with tissue to cut similar to use of a scalpel. After the tissue is removed, the blade 118 may be retracted via the slider 116 and electrosurgical energy and gas may be applied via button 114 to generate a cold plasma beam for cauterization, sterilization and/or hemostasis of the operative patient site.

In the electrosurgical cutting mode, the blade 118 is advanced and used while both electrically energized and enveloped with inert gas flow. This configuration resembles an electrosurgical knife approach, where the electrosurgical energy does the cutting. However, with the addition of the inert gas flow, cuts made show virtually no eschar, with very little collateral damage along the side walls of the cut. The cutting speed is considerably faster, with less mechanical cutting resistance as compared to when the knife blade is not electrically energized, i.e., the mechanical cutting mode. Hemostasis is also affected during this process.

Figure 5:
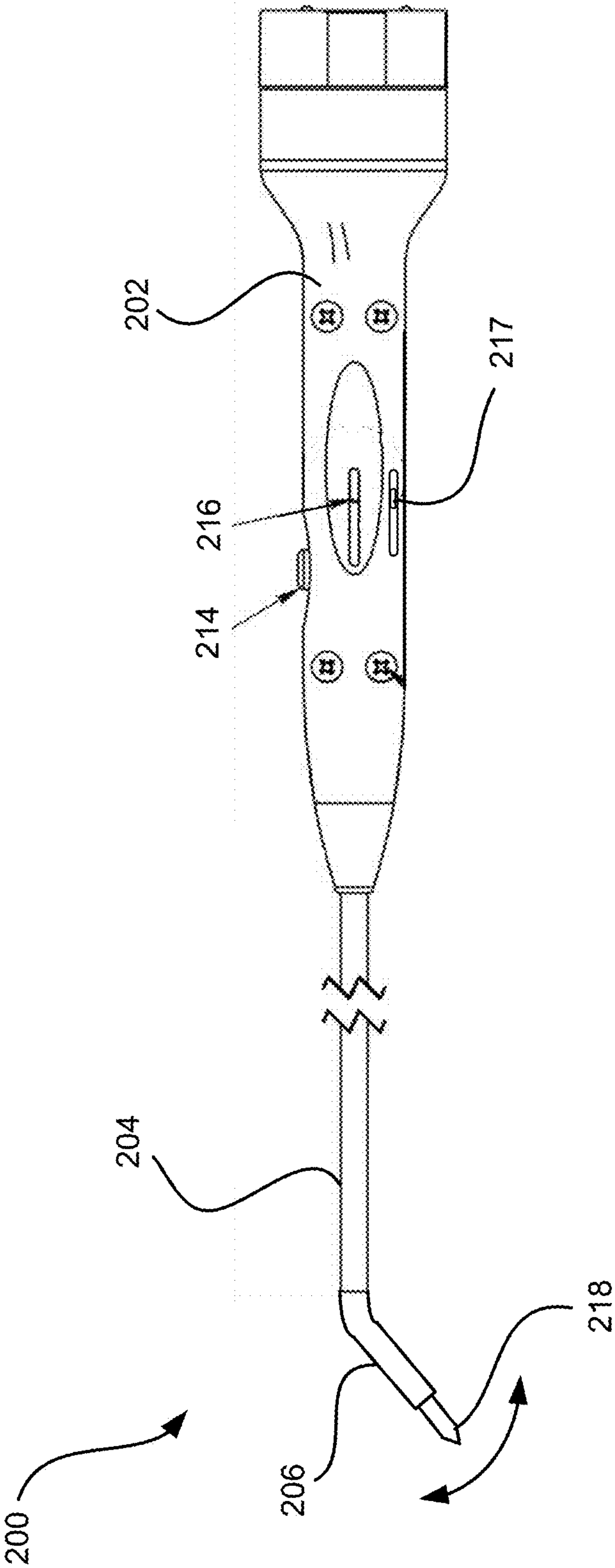
FIG. 5 illustrates an exemplary electrosurgical apparatus including an articulating distal end in accordance with an embodiment of the present disclosure.

In a further embodiment, the electrosurgical apparatus of the present disclosure will have an articulating distal end. Referring to FIG. 5, the electrosurgical handpiece 200 will have similar aspects to the embodiments described above. In this embodiment, however, the distal end 206, e.g., approximately 2 inches, is flexible to allow it to maneuver at the surgical site. An additional control 217, e.g., a slider, trigger, or the like, is provided in the proximal housing 202 to control the bending of the distal end 206. As in the above described embodiments, a button 214 is provided to apply electrosurgical energy to the blade 218 and, in certain embodiments, enable gas flow through the flow tube. Furthermore, slider 216 will expose the blade 218 at the open distal end 206 upon activation.

In one embodiment, the articulating control 217 will include two wires, one pulling to articulate and one pulling to straighten the distal end 206. The outer tube 204 will be the similar to the design shown in FIG. 2 and will be rigid, preferably made of Ultem™, Lestran™, or similar material, up to the last 2 inches which would be made of a material similar to that of a gastrointestinal (GI) flexible scope. In certain embodiments, a mesh infused Teflon™ or similar material and a flexible insulating material may be positioned inside the outer tube 204 and would allow the distal end 206 to bend at least 45° and not collapse the inner tube carrying the gas. The blade 218 will be made of a flexible metallic material such as Nitinol™ that would be able to bend but would retain its shape in the straightened position. Alternatively, a straight metal blade 218 would be provided with the distal 2 inches made of a linked metal, e.g., stainless steel, tungsten, etc., such that it would still carry a current but would be bendable and the cutting portion of the blade 218 would be attached to the distal end of the linked portion.

Figure 6:
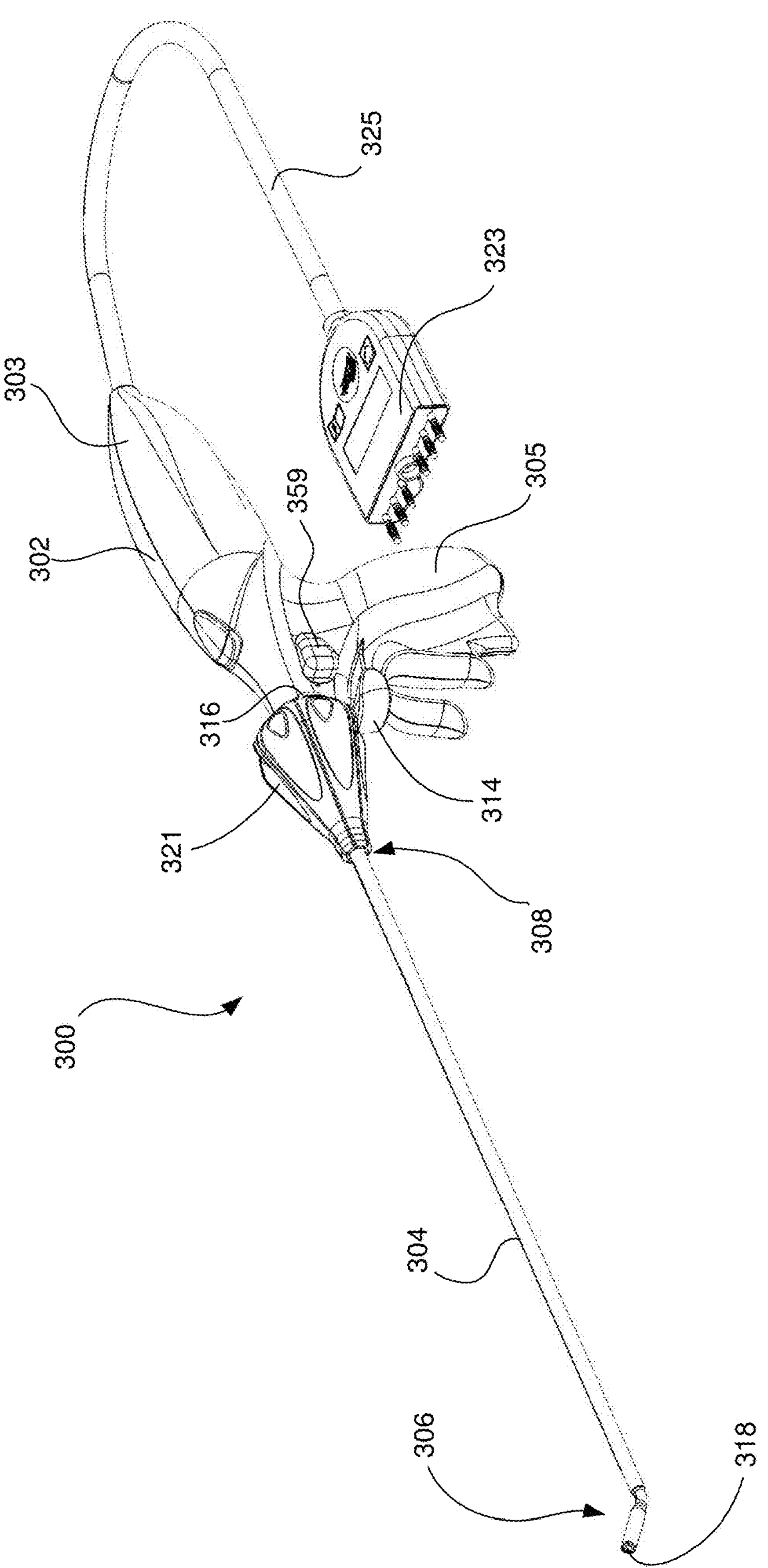
FIG. 6 is a perspective view of an electrosurgical apparatus in accordance with another embodiment of the present disclosure.

In another embodiment, an electrosurgical apparatus of the present disclosure includes a bent tip applicator or handpiece. Referring to FIG. 6, the handpiece or plasma generator 300 may be configured as a trigger-type handpiece or cold plasma bent tip applicator and will have similar aspects to the embodiments described above. In this embodiment, however, the distal end 306 is pre-bent, e.g., in certain embodiments approximately 28.72 mm, and rotatable to maneuver the distal end 306 at the surgical site 18. The handpiece 300 includes a housing 302 with a handle 305 to facilitate maneuvering of the apparatus by an operator. The handpiece 300 further includes a transformer (not shown) disposed in a proximal end 303 of the housing 302, an activation button 314 for activating the applicator or handpiece to generate plasma configured as a trigger-type button, an insulating tube 304 with a discharge electrode or blade 318 disposed therein. It is to be appreciated that in certain embodiments, the transformer is not disposed in the housing 302, but provided in an appropriate electrosurgical generator. The discharge electrode or blade 318 is coupled to a conductive metal tube (disposed within the insulating tube 304) which is further coupled to a slider button 316, collectively referred to as a slider assembly 319. The slider button 316 moves the metal tube 322 which extends or retracts the discharge electrode or blade 318 beyond the distal end 306 of the insulating tube 304. In one embodiment, the slider button 316 is moved in the distal direction to extend the electrode 318, and the electrode 318 may be retracted by actuating a spring-loaded release button 359. A knob 321 is provided at the proximal end 308 of the insulating tube 304 to enable 360-degree rotation of the insulating tube 304 and thus the distal end 306 of the applicator. It is to be appreciated that the distal end 306 rotates at a predetermined angle relative to the longitudinal axis of the insulating tube 304. Additionally, a connector 323 is provided for coupling the applicator to an electrosurgical generator. In certain embodiments, the connector 323 receives electrosurgical energy and gas which it provides to the applicator or apparatus 300 via cable 325.

As described above, the system of the present disclosure includes an electrosurgical generator unit (ESU), a handpiece (e.g., handpiece 14, 100, 200, 300), and a supply of helium gas. Radiofrequency (RF) energy is delivered to the handpiece by the ESU and used to energize an electrode. When helium gas is passed over the energized electrode, a helium plasma is generated which allows for conduction of the RF energy from the electrode to the patient in the form of a precise helium plasma beam. The energy delivered to the patient via the helium plasma beam is very precise and cooler in temperature in comparison to other surgical energy modalities such as laser and standard RF monopolar energy. In one embodiment, helium is used because it can be converted to a plasma with very little energy. The result is an energy that is unique in its ability to provide tissue heating and cooling almost simultaneously. With the devices and systems of the present disclosure, less than 0.1% of the helium gas employed is converted to plasma, so >99.9% of the helium remains in a gaseous state. Helium is eight times more thermally-conductive than air, so the unconverted, or un-ionized, helium flows across the tissue to draw away excess heat, minimizing any unintended thermal effect. It is to be appreciated that although helium is used in the above described embodiment, inert gases other than helium may be used with the embodiments of the present disclosure.

The unique heating of the devices and systems of the present disclosure makes it a useful surgical tool for the coagulation of subcutaneous soft tissue similar to the LAL and RFAL devices discussed above. As the tip of the handpiece or plasma generator is drawn through the subdermal plane, heating of the tissue results in instant coagulation and contraction of the tissue followed by immediate cooling.

Figure 7:
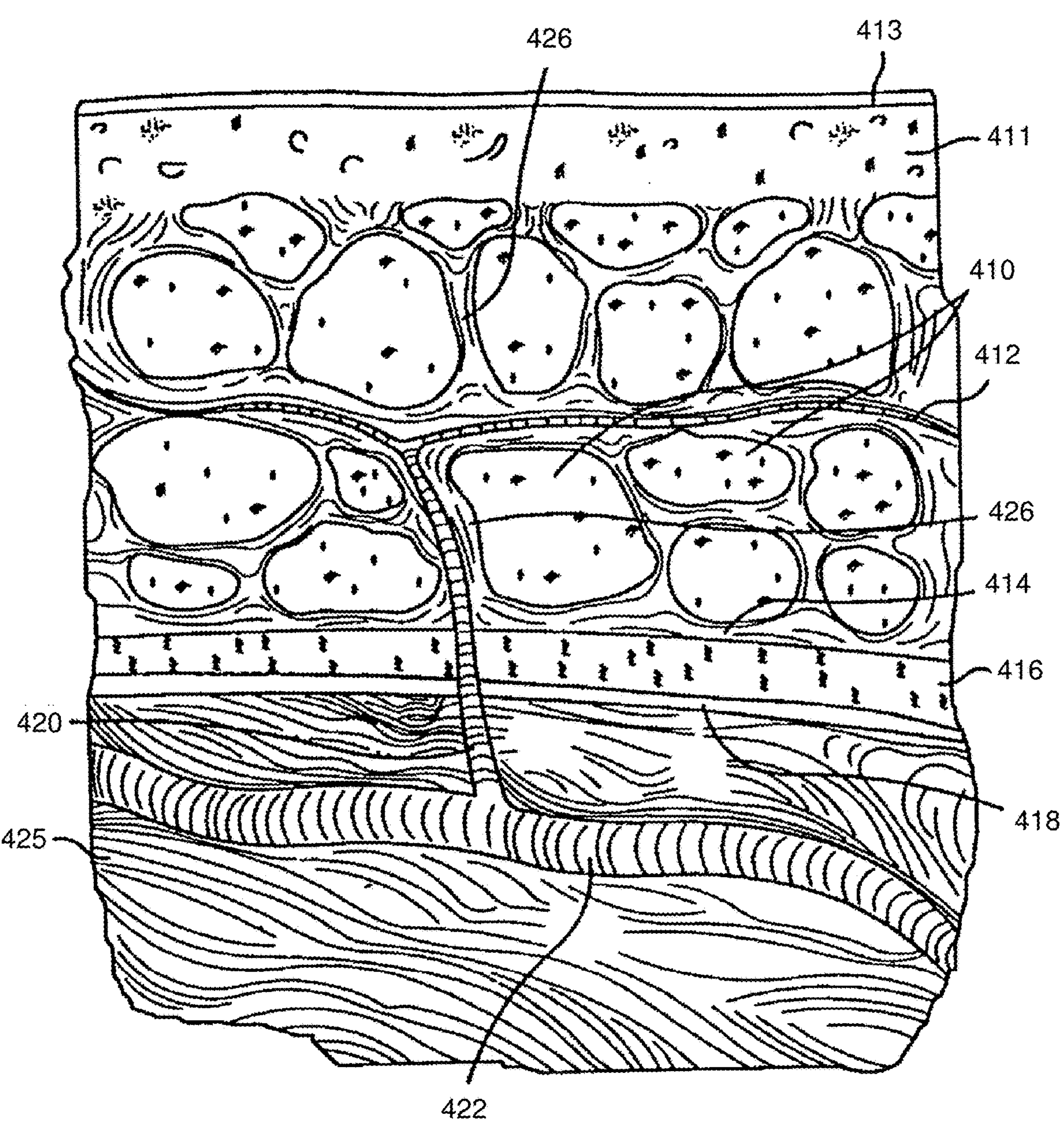
FIG. 7 is a cross-sectional view of the anatomy of human cutaneous tissue.

Turning now to FIG. 7, a cross-sectional view of the anatomy of the human cutaneous tissue is illustrated. An epidermis layer 413 overlies the dermis layer 411. Underneath the dermis 411 is a layer of subcutaneous fat 410. Superficial vessels 412 within the fat layer 410 are connected to perforating vessels 420 which in turn are connected to deep vessels 422. Vertical cutaneous ligaments 426 joining tissue layers, are also shown within the fat layer 410. Muscle 425 is covered by a thin layer of deep fascia 418. The fat layer 410 is sheathed by a thin layer of superficial fascia 414. A naturally occurring tissue plane or fascial cleft 416 occurs between the superficial fascia 414 and deep fascia 418.

Figure 8:
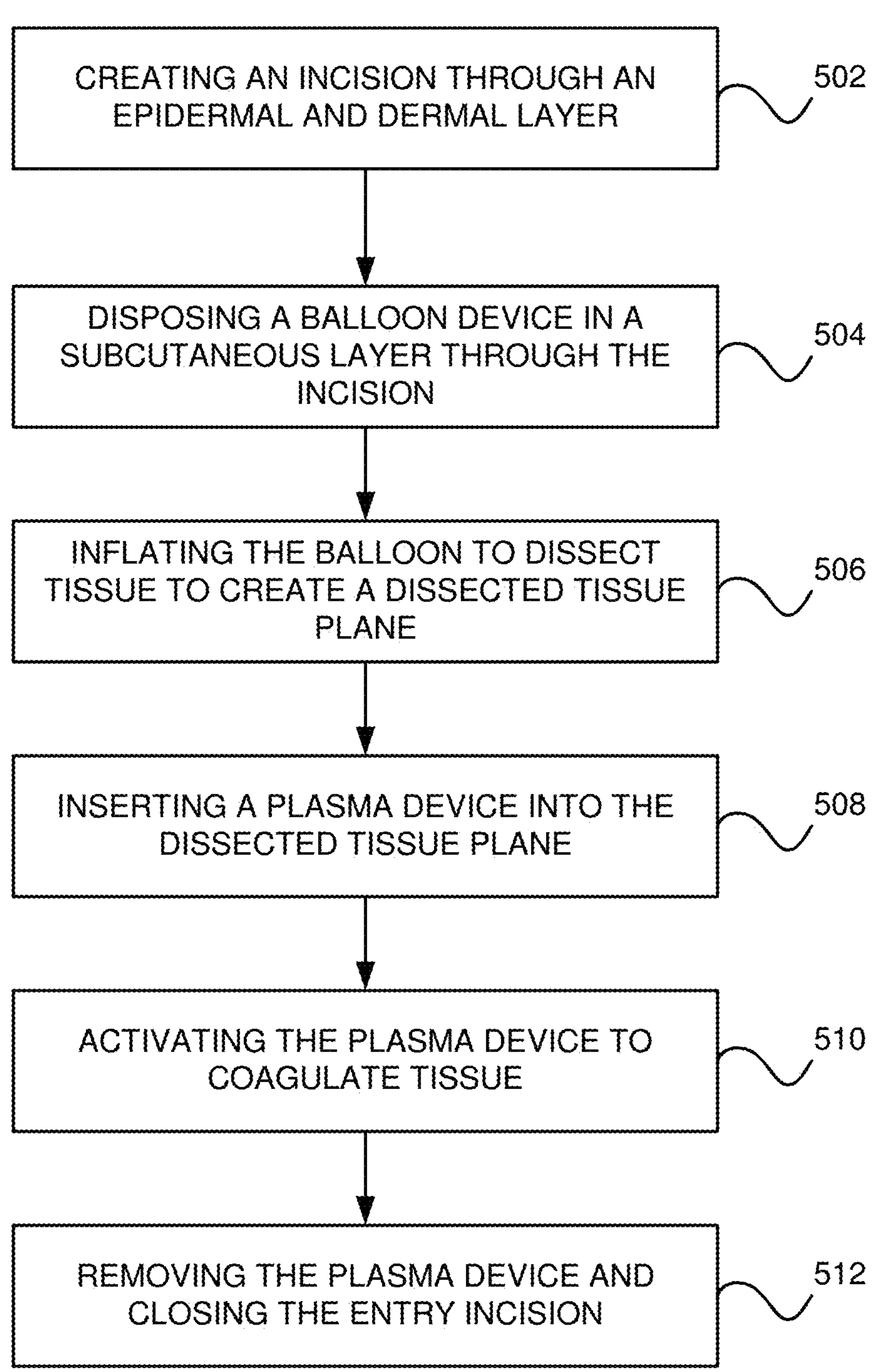
FIG. 8 is a flowchart illustrating an exemplary method for tightening tissue in accordance with an embodiment of the present disclosure.

A method of coagulating a subcutaneous layer of tissue will now be described in relation to FIG. 7 and FIG. 8. It is to be appreciated that method may be employed with any of the handpieces or plasma generators described above, for example, plasma generators 14, 100, 200, 300.

Initially, in step 502, an incision, i.e., an entry incision, is created through the epidermal 413 and dermal 411 layers of a patient at a location appropriate for a particular procedure. A balloon device is then disposed in a subcutaneous layer 410 through the incision, in step 504. The balloon may be carried by or otherwise associated with a tunneling member, such as being rolled or folded alongside or about the tunneling member. The tunneling member may be a rod or, may be a hollow tube adapted to receive a laparoscope or the like. In one embodiment, a deflated, rolled balloon is disposed about the distal end 106, 206, 306 and/or shaft of any one of the plasma devices 14, 100, 200, 300 described above and is tunneled bluntly to a desired location within the body.

Next, in step 506, the balloon is inflated to dissect tissue to create a dissected tissue plane. The balloon may be inflated by any suitable inflation medium, such as but not limited to saline or air. In one embodiment, the inflation medium is supplied via the tunneling member. In another embodiment, helium supplied from the plasma generator may be used to inflate the balloon. For example, the distal tip 106, 206, 306 of the handpiece or plasma generator 100, 200, 300 may be connected or coupled to inflation tubing on the balloon and the helium that is released from the tip is used to inflate the balloon. In certain embodiments, the deflated, rolled balloon is coupled via the inflation tubing to the tip of the plasma generator before being disposed about the distal end 106, 206, 306. The plasma generator with balloon is then tunneled bluntly to a desired location and a flow of helium is provided through the plasma generator to inflate the balloon. The deployed balloon dissects the tissue along a naturally occurring tissue plane to dissect the tissue in a less traumatic manner than mechanical dissection. In addition, pressure from the balloon against the dissected tissue creates a tamponade effect that helps reduce bleeding and promote favorable cosmesis.

In step 508, the plasma generator is inserted into the dissected tissue plane. It is to be appreciated that if a tunneling member is employed to place the balloon, the tunneling member and balloon preferably are removed before inserting the plasma generator. Additionally, if the plasma generator is employed to place the balloon, only the balloon will be removed after the dissected tissue plane is created. Next, in step 510, the plasma generator 100, 200, 300 is activated to coagulate tissue to (i) tighten tissue (ii) shrink tissue and/or (iii) contour or sculpt the body. After the desired effects are achieved, the plasma generator is removed and the entry incision is closed, in step 512.

Alternate configurations for inserting the balloon and plasma device are contemplated, such as configurations in which (i) the balloon and plasma device are inserted together, the balloon is deployed and remains in place in a deflated or inflated or partially inflated condition to facilitate distribution of plasma from the plasma device during treatment, (ii) the balloon is inserted first, separate from the plasma device, and is deflated and removed before inserting the plasma device, (iii) the balloon is inserted and inflated to dissect tissue, and then the plasma device is inserted through a cannula of the balloon device to deliver plasma treatment, with or without removing or deflating the balloon, and (iv) the balloon is inserted and inflated to dissect tissue, and then the plasma device is inserted through a cannula of the balloon device to deliver plasma treatment, with the balloon device removed after the plasma device is in place, such as by having a split line along the length of the tube through which the plasma device is inserted and to which the balloon is attached. If the balloon is left in place in an inflated or partially inflated condition during a portion of the plasma treatment, space may be created at the edges of the dissection to promote flow of plasma to the extremities of the space created. According to one embodiment, the balloon is left fully or partially inflated for an initial portion of the plasma treatment to promote distribution of the gas to the edges of the dissected area, and the balloon is thereafter removed during the remainder of the plasma treatment. A wanding motion may be used with the plasma device, moving the tip back and forth and laterally in order to optimize distribution of the helium gas, plasma and energy to achieve the desired tissue tightening, coagulation, shrinking or sculpting. Custom tips for the plasma generators of the present disclosure are contemplated to optimize gas and energy distribution. See, for example, commonly-owned U.S. patent application Ser. No. 15/717,643 filed Sep. 27, 2017 entitled "DEVICES, SYSTEMS AND METHODS FOR ENHANCING PHYSIOLOGICAL EFFECTIVENESS OF MEDICAL COLD PLASMA DISCHARGES" and commonly-owned PCT Patent Application No. PCT/US2016/064537 filed Dec. 2, 2016 entitled "DEVICES, SYSTEMS AND METHODS FOR IMPROVED MIXING OF COLD PLASMA BEAM JETS WITH AMBIENT ATMOSPHERE FOR ENHANCED PRODUCTION OF RADICAL SPECIES, the entire contents of both of which is hereby incorporated by reference.

As discussed above, an RF waveform flows through the conductive plasma beam generated by the plasma generator. This conductive plasma beam can be thought of as a flexible wire or electrode that "connects" to the tissue that represents the path of least resistance for the flow of the RF energy. The tissue that represents the path of least resistance is typically either the tissue that is in closest proximity to the tip of the plasma generator or the tissue that has the lowest impedance, i.e., tissue that has the lowest impedance relative to adjacent tissue. This means that the energy from the plasma generator is not directed or focused in any set direction when activated in the subdermal plane as in some RFAL devices but finds the tissue that represents the path of least resistance surrounding the tip of the plasma generator. In other words, the energy from the tip of the plasma generator may be directed in a linear direction (relative to the shaft of the plasma generator) from the tip, above the tip, below the tip, adjacent either side of the tip and anywhere inbetween effectively providing energy in 360 degrees about the tip.

If the path of least resistance is through the overlying dermis, the plasma energy will be directed to the dermis. If the path of least resistance is through the fibroseptal network, the plasma energy will be directed there. As the tip of the plasma generator is drawn through the subdermal plane, the path of least resistance in the surrounding tissue is constantly changing. As the energy is constantly finding a new preferred path, the plasma beam quickly alternates between treating the different tissue surrounding the tip of the device. This allows for 360° tissue treatment without the need for the user to redirect the flow of energy.

Since the fibroseptal network (FSN) is typically the closest tissue to the tip of the plasma generator 100, 200, 300, the vast majority of the energy delivered by the plasma generator device results in coagulation and contraction of the fibroseptal bands. Published studies have shown that the soft tissue contraction induced by RFAL devices is due to its effect on the FSN. Therefore, maximizing the energy flow to the FSN expedites the soft tissue contraction process.

However, it is to be appreciated that not all RF is created equal. Very different tissue effects can result at the same power setting by simply changing from a waveform designed for cutting to a waveform designed for coagulation. The RF waveform of the plasma generator 100, 200, 300 has lower current than other RF devices. In most cases, the current of the plasma generator 100, 200, 300 is an order of magnitude lower. Exemplary waveforms are shown and described in commonly-owned PCT Patent Application No. PCT/US2017/062195 filed Nov. 17, 2017 entitled "ELECTROSURGICAL APPARATUS WITH DYNAMIC LEAKAGE CURRENT COMPENSATION AND DYNAMIC RF MODULATION" and PCT Patent Application No. PCT/US2018/015948 filed Jan. 30, 2018 entitled "ELECTROSURGICAL APPARATUS WITH FLEXIBLE SHAFT", the entire contents of both of which is hereby incorporated by reference.

The current of the plasma generator waveform flows through the conductive plasma beam to create additional heating of the target tissue. However, since the current is so low, it is not able to penetrate deep into the tissue. This allows for soft tissue heating with minimal depth of thermal effect. This also prevents tissue from being overtreated in the subdermal application. Previously treated tissue has higher impedance. Low current cannot push through the higher impedance tissue. The energy preferentially treats the previously untreated tissue since it is the path of least resistance. This prevents overtreating any one particular area and maximizes the treatment of untreated tissue.

Figure 12:
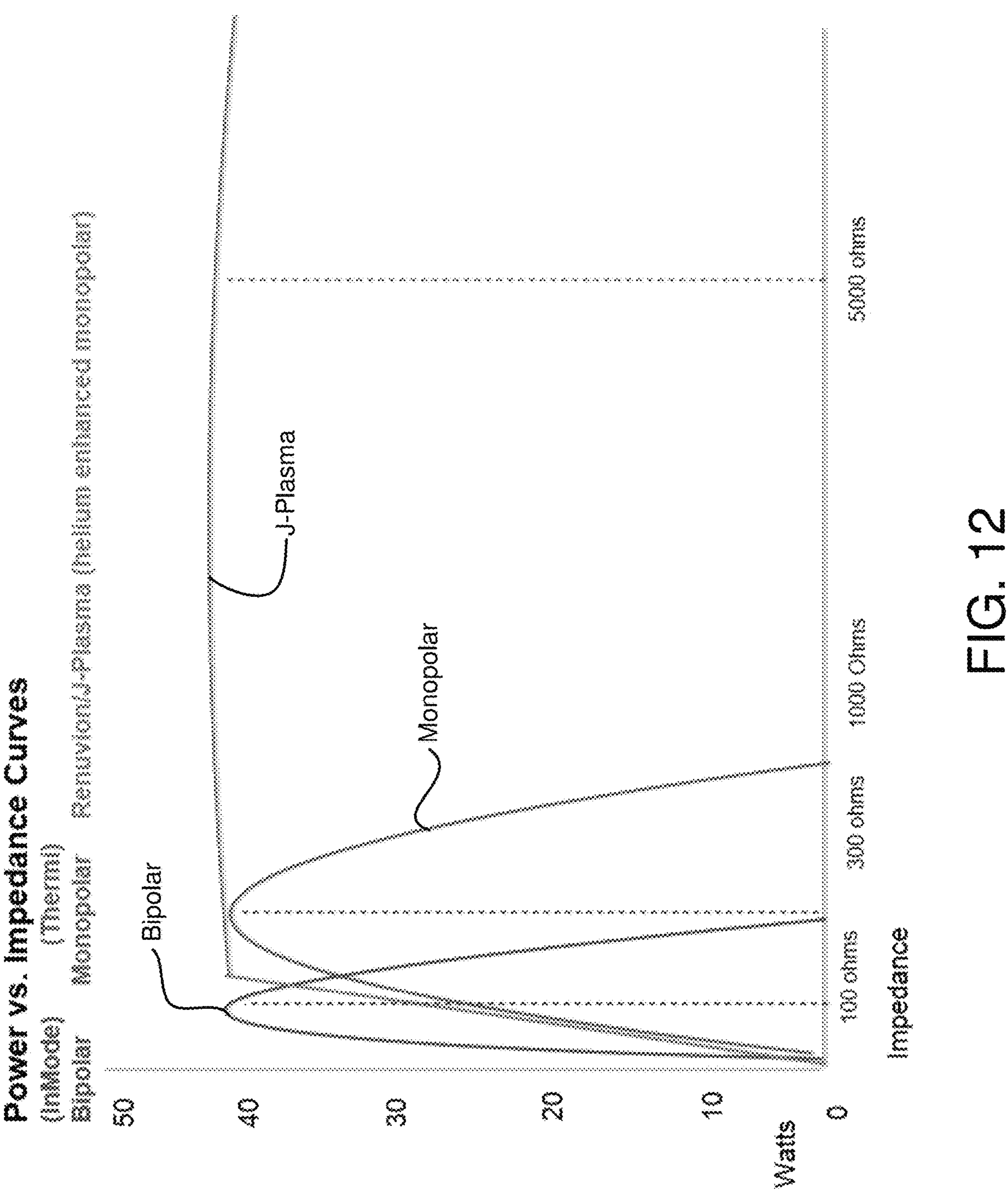
FIG. 12 illustrates power versus impedance curves for various devices.

The design of the electrosurgical generator unit for the plasma generator of the present disclosure is fundamentally different from monopolar and bipolar devices. In one embodiment, the electrosurgical generator is configured to apply power based on impedance determined (e.g., by at least one processor of the generator using data gathered by one or more sensors of the generator) at the output of the electrosurgical generator. As shown in the in FIG. 12, monopolar and bipolar devices are configured to have limited power output in tissues with higher impedance, such as fat. Electrosurgical generators coupled to such monopolar and bipolar devices are programmed, e.g., hardwired or software-based, to follow the curves illustrated in FIG. 12. The plasma generator of the present disclosure is configured to maintain consistent power output over a wide range of impedances, as shown in FIG. 12 by the curve labeled J-Plasma. For example, the plasma generator applies a constant or predetermined output power level, e.g., approximately 40 watts, over a range of tissue impedances, e.g., 150 ohms to at least 5000 ohms. When used for the coagulation and tightening of subdermal tissue, the plasma generator of the present disclosure is not self-limiting and will provide unencumbered delivery of power regardless of the tissue impedance.

Because of the points discussed above, the devices, systems and methods of the present disclosure do not require full thickness heating of the tissue being treated. It effectively and efficiently treats the target tissue, e.g., the FSN. Some devices work on the principal of full thickness tissue heating. In these devices, the energy is primarily directed into the dermis and the device is activated until a pre-set epidermal temperature is achieved and maintained across the entire thickness or volume of the tissue. Although these devices have proven effective in achieving soft tissue contraction, full thickness tissue heating is not the only method or the most time efficient method for achieving soft tissue contraction through coagulation. The plasma generator of the present disclosure achieves soft tissue coagulation and contraction by heating tissue for very short periods of time followed by immediate cooling. This allows for immediate coagulation and contraction of the tissue with very limited depth of thermal effect, as compared to other surgical devices as shown in FIG. 11. Since the plasma generator of the present disclosure works on the scientific principle of the path of least resistance, the vast majority of the energy from the device results in coagulation and contraction of the FSN, which is the tissue in closest proximity to the tip of the device. The plasma generator of the present disclosure focuses delivery of its energy on immediate heating of the FSN, which results in immediate soft tissue contraction without unnecessarily heating the full thickness of the dermis.

The balloons of the present disclosure can be shaped to dissect tissue in a configuration that corresponds to the area to be tightened, coagulated or contoured. By way of example, the balloon may be an inelastic balloon of predetermined shape, where the shape corresponds to the area to be dissected. Although less preferred because it provides less control, an elastic balloon may be used. In one configuration, the balloon is generally be shaped to dissect one side of the abdomen. The balloon may be used twice, first on one side then flipped over to do the other side. Balloons may be shaped for buttocks, arms, legs, neck, forehead, chin, or any other body part or area so that the balloon deploys and dissects a specific area of tissue. Different sizes of configurations could be provided too.

Figures 9A, 9B:
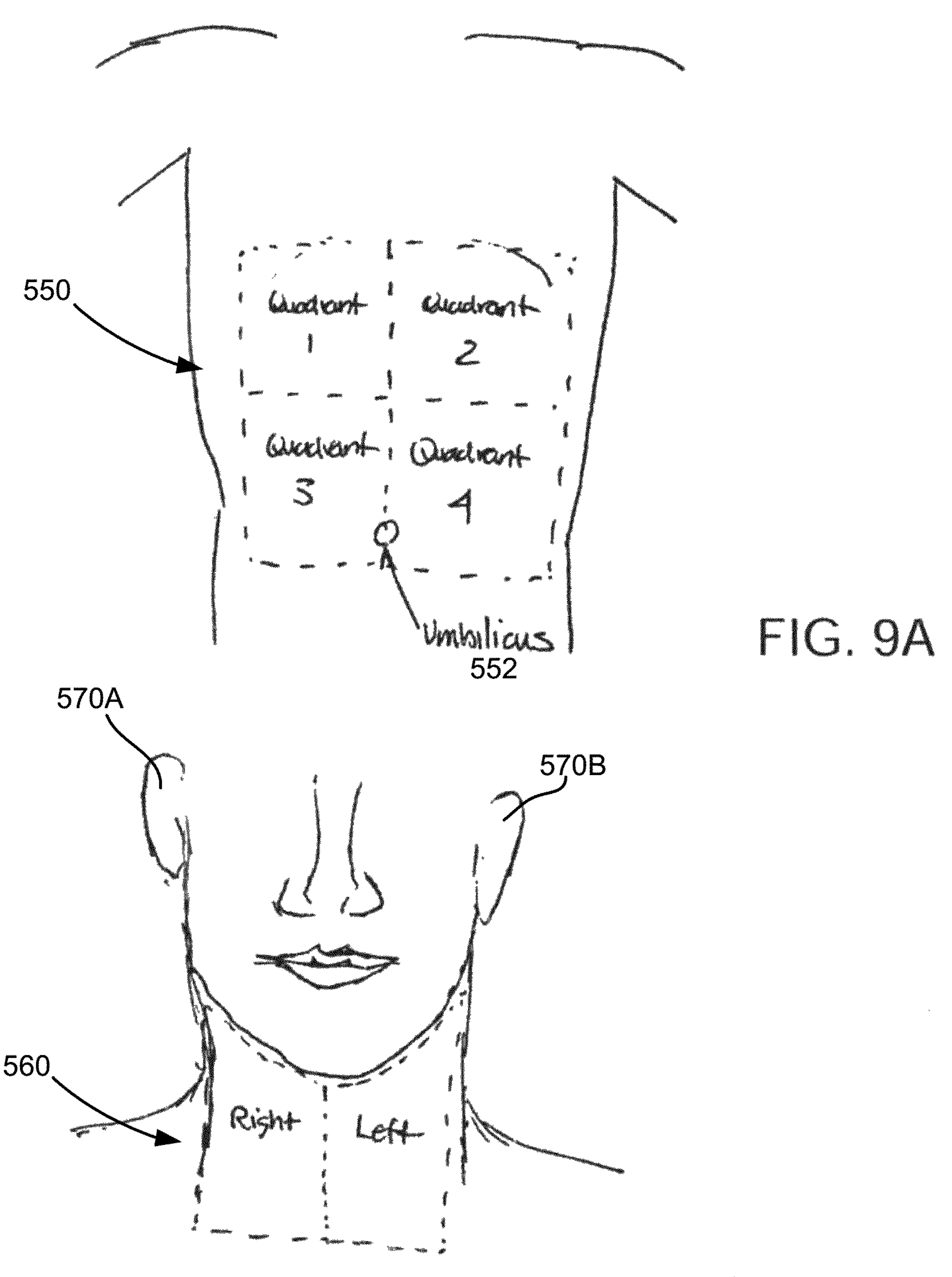
FIGS. 9A and 9B are views of portions of human anatomy illustrating placement locations for a dissecting balloon in accordance with an embodiment of the present disclosure.

Referring to FIGS. 9A and 9B, portions of human anatomy illustrating placement locations for a dissecting balloon in accordance with an embodiment of the present disclosure are illustrated, where FIGS. 10A-10J illustrate dissecting balloons of various shapes and sizes in accordance with embodiments of the present disclosure.

Figure 10A:
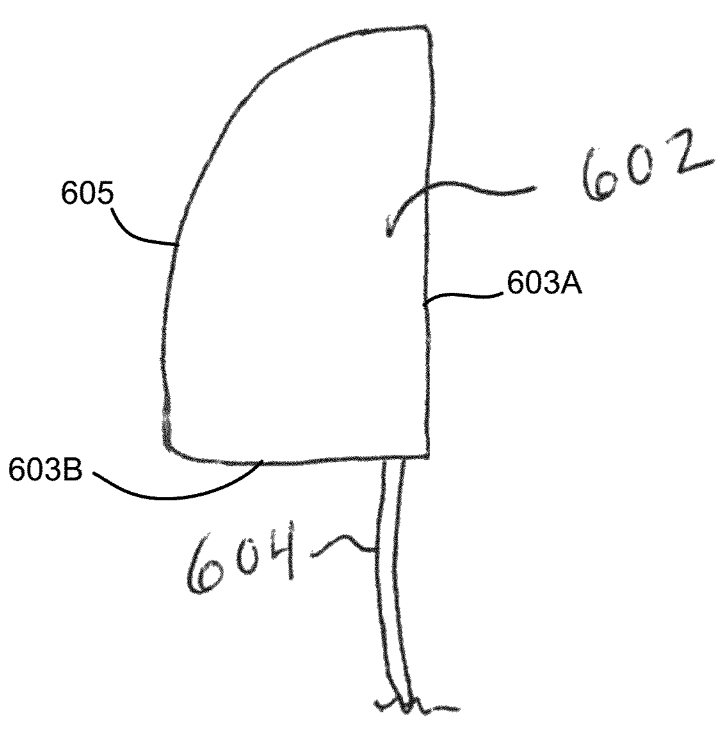
FIGS. 10A-10J illustrate dissecting balloons of various types and sizes in accordance with an embodiment of the present disclosure.

FIG. 9A shows an abdomen 550 separated into four quadrants, labeled quadrants 1-4, for possible placement of a dissecting balloon. FIG. 10A illustrates a balloon 602 shaped and configured for placement at either quadrant 1 and/or quadrant 2 of abdomen 550. It is to be appreciated that balloon 602 is shaped to conform to the shape of the particular quadrant that balloon 602 will be placed (e.g., quadrant 1 or 2). The balloon 602 further includes an inflation tube 604, which may be routed through the umbilicus 552 of abdomen 550. In one embodiment, balloon 602 includes generally linear edges or sides 603A, 603B and a curved surface or side 605, where edges 603A, 603B and surface 605 are configured such that when balloon 602 is inflated within abdomen 550 via tube 604, the shape of balloon 602 conforms to quadrant 1 or 2. Tube 604 is positioned at a corner joining edges or sides 603A, 603B for placement at umbilicus 552, such that when balloon 602 is inflated within abdomen 550, balloon 602 expands in a direction that fills the space of quadrant 1 or 2. It is to be appreciated that to place balloon 602 in quadrant 1, balloon 602 is oriented as shown in FIG. 10A with curved surface 605 disposed to the left of edge 603A. To place balloon 602 in quadrant 2, balloon 602 is rotated or flipped over from the orientation shown in FIG. 10A such that surface 605 is disposed to the right of edge 603A.

Figure 10B:
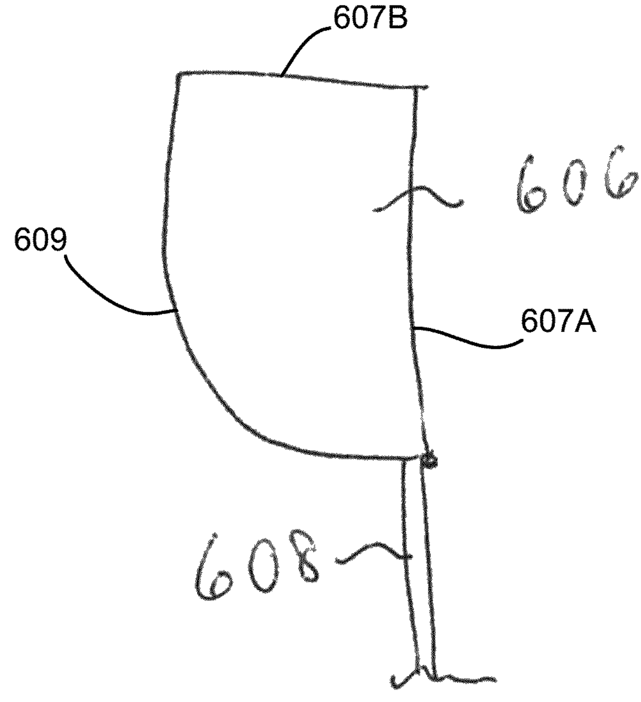

FIG. 10B illustrates a balloon 606 shaped and configured for placement at either quadrant 3 and/or quadrant 4 of abdomen 550, where the balloon 606 includes inflation tube 608. In one embodiment, balloon 606 includes generally linear edges or sides 607A, 607B and a concavely curved surface or side 609, where edges 607A, 607B and surface 609 are configured such that when balloon 606 is inflated within abdomen 550 via tube 608, the shape of balloon 606 conforms to quadrant 3 or 4. Tube 608 is positioned at a corner joining edge 607A and surface 609 for placement at umbilicus 552, such that when balloon 606 is inflated within abdomen 550, balloon 606 expands in a direction that fills the space of quadrant 3 or 4. It is to be appreciated that to place balloon 606 in quadrant 3, balloon 606 is oriented as shown in FIG. 10B with curved surface 609 disposed to the left of edge 607A. To place balloon 606 in quadrant 4, balloon 606 is rotated or flipped over from the orientation shown in FIG. 10B such that surface 609 is disposed to the right of edge 607A.

In one embodiment, balloons 602, 606 are each configured to be ¼ the size of abdomen 550.

Figure 10C:
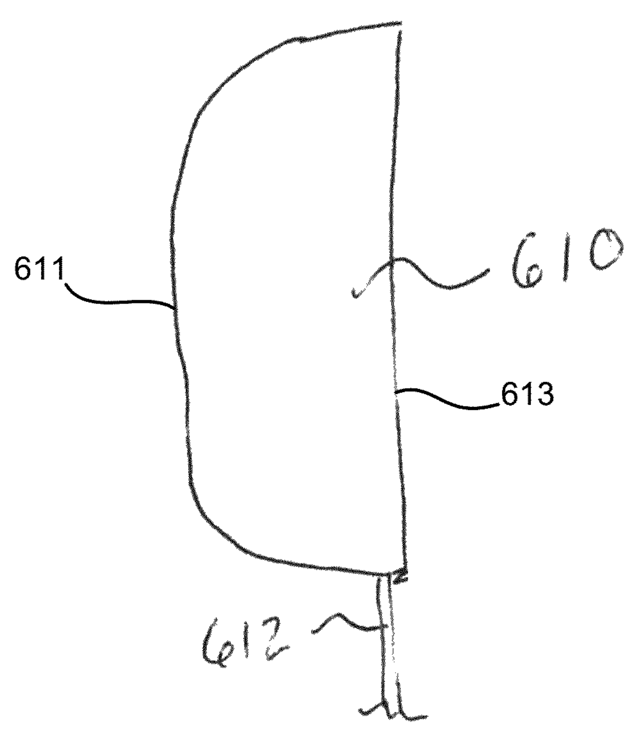

FIG. 10C illustrates a balloon 610 shaped and configured for placement at either quadrant 1 and 3 at the same time and/or quadrants 2 and 4 at the same time of abdomen 550, where the balloon 610 includes inflation tube 612, a generally linear side 613, and a concavely curved surface 611, which is coupled to each end of edge 613 and extends away from edge 613. Tube 612 is positioned at a corner joining edge 613 and surface 611 for placement at umbilicus 552, such that when balloon 610 is inflated within abdomen 550, balloon 610 expands in a direction that fills the space of quadrants 1 and 3 or quadrants 2 and 4. It is to be appreciated that to place balloon 610 in quadrants 1 and 3, balloon 610 is oriented as shown in FIG. 10C with curved surface 611 disposed to the left of edge 613. To place balloon 610 in quadrants 2 and 4, balloon 610 is rotated or flipped over from the orientation shown in FIG. 10C such that surface 610 is disposed to the right of edge 613. In one embodiment, balloon 610 is half the size of abdomen 550.

Figure 10D:
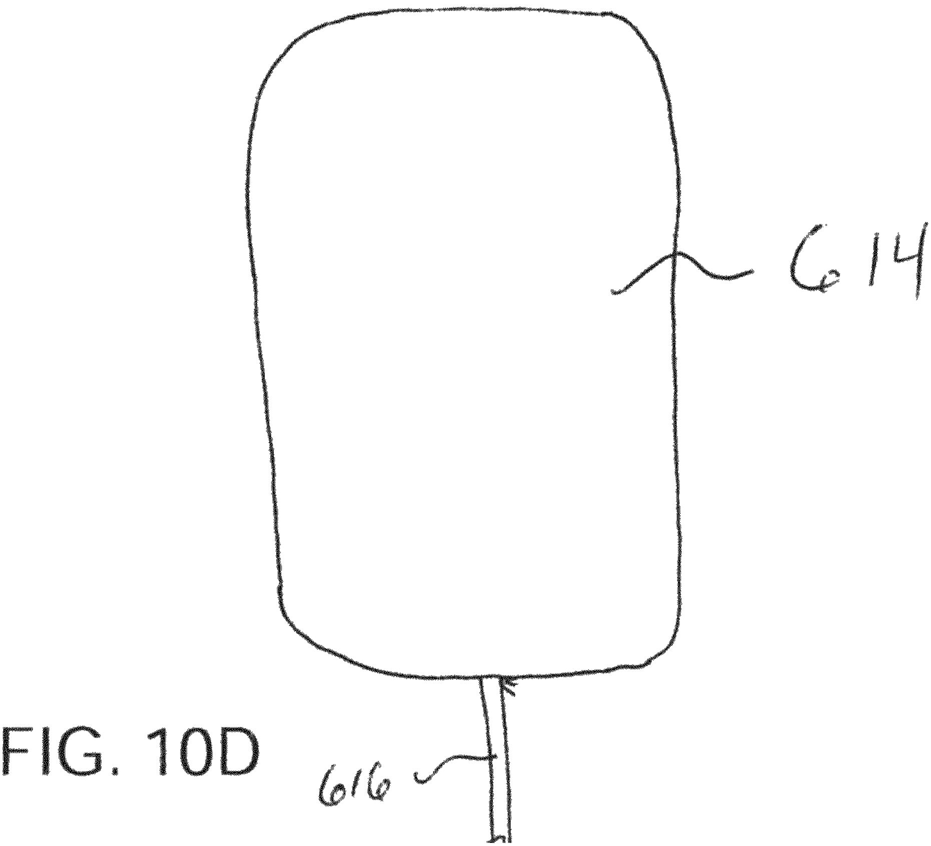

FIG. 10D illustrates a balloon 614 shaped and configured for placement at all four quadrants simultaneously. Balloon 614 further includes inflation tube 616, which is positioned for placement at umbilicus 552 such that when balloon 614 is inflated within abdomen 550, balloon 614 expands in a direction that fills the space of all four quadrants. It is to be appreciated that, in one embodiment, balloon 614 is approximately the same size of abdomen 550 and is configured in a generally rectangular shape with curved corners.

Figures 10E, 10F, 10G:
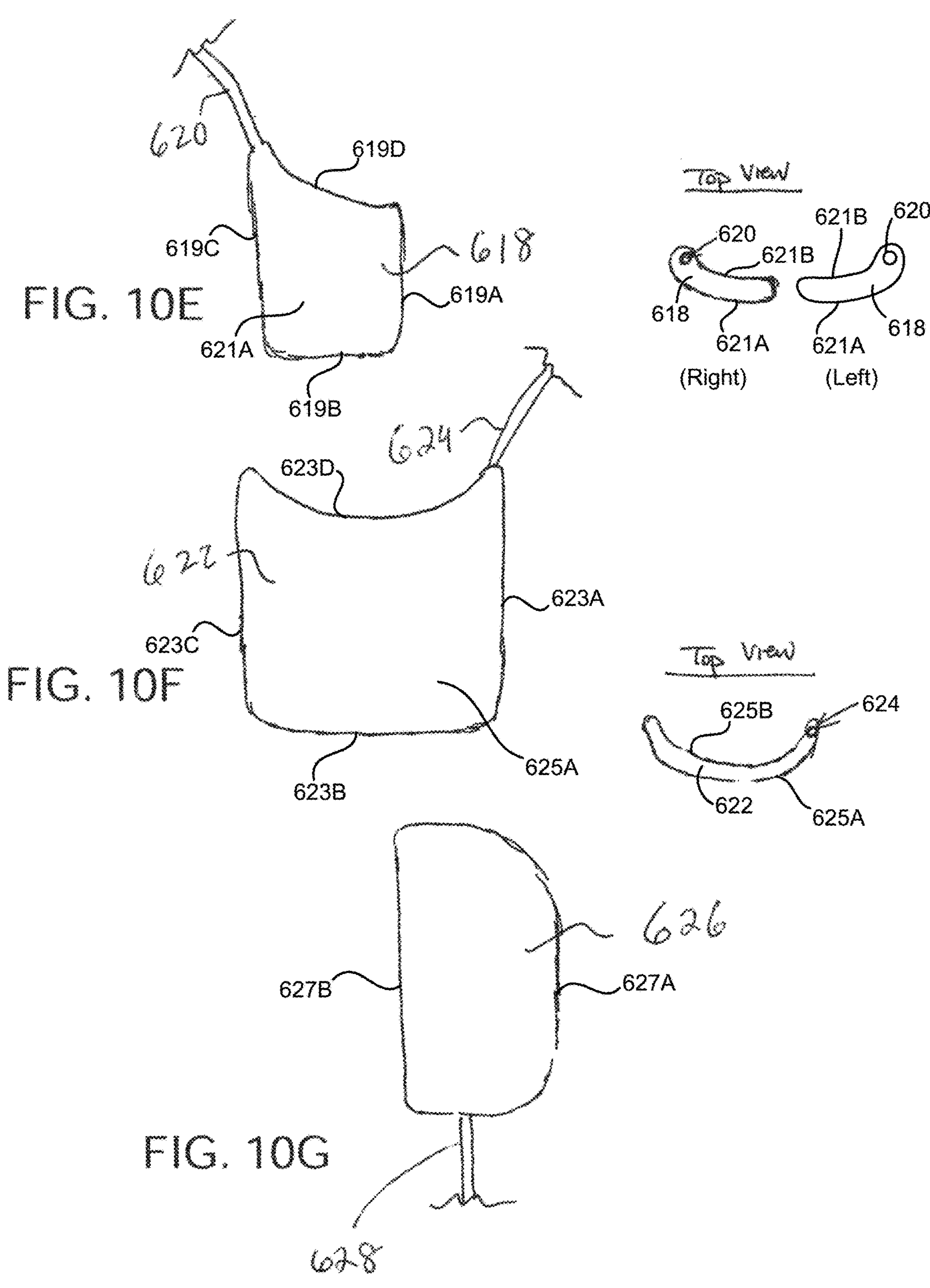

FIG. 9B shows a neck 560 divided into left and right portions for placement of a dissecting balloon. FIG. 10E illustrates a balloon 618 shaped and configured for placement at either the left side or right side of the neck 560. It is to be appreciated that balloon 618 is shaped to conform to the shape of either the left or right side of the neck 560. Balloon 618 includes sides or edges 619A-D and surfaces 621A, 621B (where surfaces 621A, 621B are shown in the top view of FIG. 10E). Sides 619A-C are generally linear, where sides 619A, 619C are parallel to each other and perpendicular to side 619B. Side 619C is longer than side 619A and side 619D is configured in a concavely curved shape, such that side 619D slopes in a concavely curved path from an end of side 619A to an end of side 619C. The balloon 618 further includes an inflation tube 620 which may be coupled to the balloon 618 so as to be routed near the right ear 570A or left ear 570B of a patient. In one embodiment, opposite surfaces 621A, 621B of balloon 618 are each configured in a generally flat planar shape and are parallel to each other. In this embodiment, balloon 618 is oriented as shown in FIG. 10E to be placed in the right portion of neck 560. Balloon 618 may be flipped with respect to the orientation of FIG. 10E to be placed in the left portion of neck 560. In another embodiment, opposite surfaces 621A, 621B of balloon 618 are each configured in a curved shape (e.g., where side 621A is convexly curved and side 621*b* is concavely curved) to wrap around right or left portion of neck 560 as shown in the top view of FIG. 10E. In this embodiment, balloon 618 may be configured as a balloon for use on the right portion of neck 560 or the left portion of neck 560 depending on the placement of tube 620 with respect to balloon 618 as shown in the top view of FIG. 10E.

FIG. 10F illustrates a full-sized balloon 622 shaped and configured for placement at the left side and right side of the neck 560 simultaneously. It is to be appreciated that balloon 622 is shaped to conform to the shape of both the left and right side of the neck 560 at the same time. Balloon 622 includes sides or edges 623A-D and surfaces 625A, 625B (where surfaces 625A, 625B are shown in the top view of FIG. 10F). Sides 623A-C are generally linear, where sides 619A, 619C are parallel to each other and perpendicular to side 619B. Side 623D is configured in a concavely curved shape and is coupled to an end of side 623A to an end of side 623C. The balloon 622 further includes an inflation tube 624 which may be coupled to the balloon 622 so as to be routed near the left ear 570A or the right ear 570B of a patient. In one embodiment, opposite surfaces 625A, 625B of balloon 622 are each configured in a generally flat planar shape and are parallel to each other. In another embodiment, opposite surfaces 625A, 625B of balloon 622 are each configured in a curved shape (e.g., where side 625A is convexly curved and side 625B is concavely curved) to wrap around neck 560 as shown in the top view of FIG. 10F.

It is to be appreciated that other shapes of dissecting balloons are contemplated to be within the scope of the present disclosure.

For example, FIG. 10G illustrates balloon 626 shaped and configured for placement at a buttock. Balloon 626 includes generally linear side or edge 627B and convexly curved side or edge 627A, where edges 627A, 627B are coupled at respective ends such that edge 627B extends away from edge 627A. Balloon 626 includes an inflation tube 628, which is positioned for placement in the fold between the buttock and thigh of a patent.

Figures 10H, 10I, 10J:
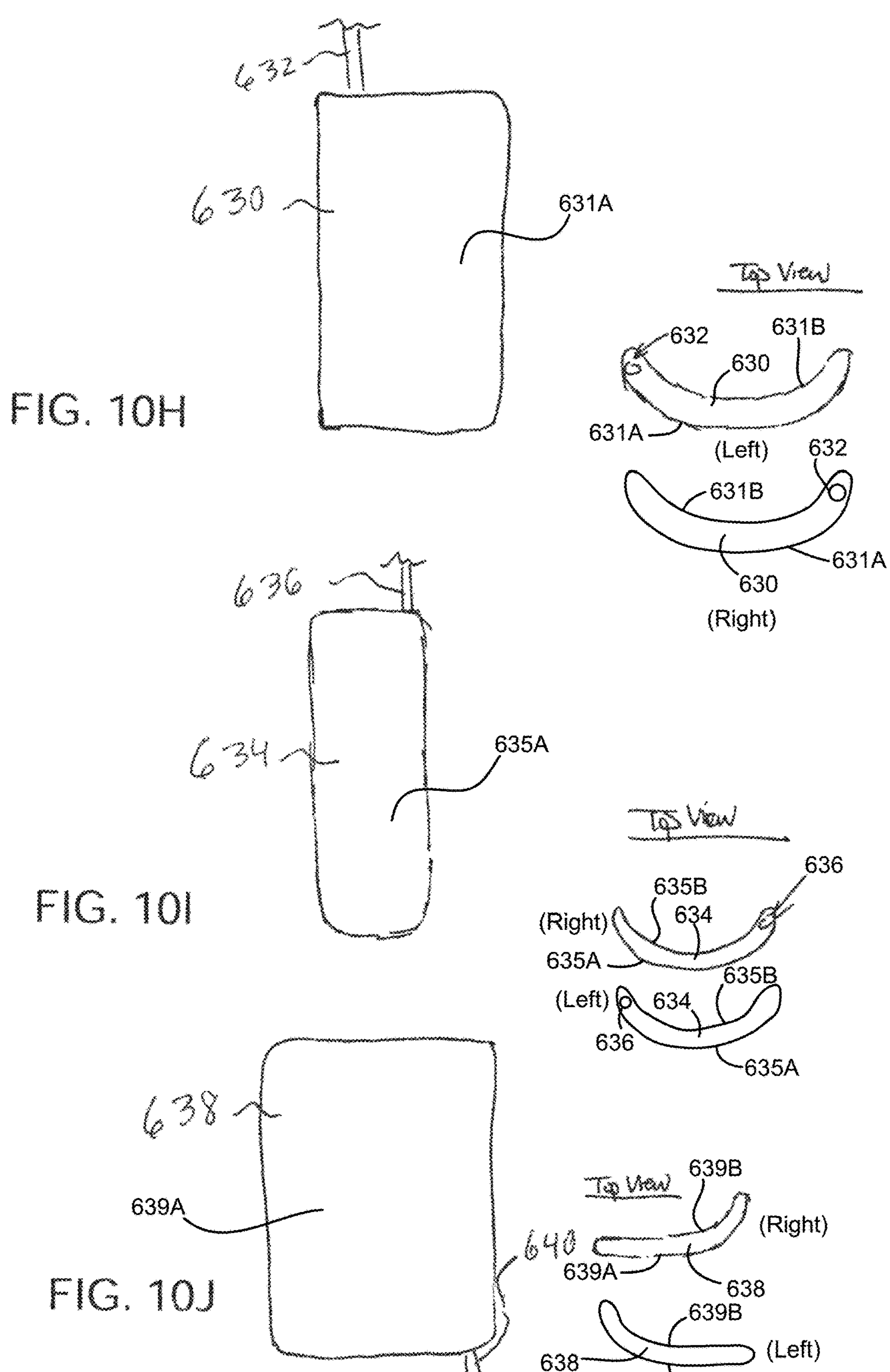

FIG. 10H illustrates balloon 630 shaped and configured for placement at a thigh of a patient. In one embodiment, balloon 630 is configured in a generally rectangular shape having curved edges and opposite surfaces or sides 631A, 631B (where surfaces 631A, 631B are shown in the top view of FIG. 10H). Balloon 630 includes an inflation tube 632, which is position for placement at either the knee or fold between the thigh (that balloon 630 is being used with) and pubic area of a patient. In one embodiment, surfaces 631A, 631B of balloon 630 are each configured in a generally flat planar shape and are parallel to each other. In this embodiment, balloon 630 may be flipped with the respect to the orientation shown in FIG. 10H to be used for the right or left thigh of the patient. In another embodiment, opposite surfaces 631A, 631B of balloon 630 are configured in a curved shape (e.g., where side 631A is convexly curved and side 631B is concavely curved) to wrap around right or left thigh of the patient as shown in the top view of FIG. 10H. In this embodiment, balloon 630 may be configured as a balloon for use on the right thigh or left thigh depending on the placement of tube 632 with respect to balloon 630 as shown in the top view of FIG. 10H.

FIG. 10I illustrates balloon 634 shaped and configured for placement at an arm of a patient. In one embodiment, balloon 634 is configured in a generally rectangular shape having curved edges and opposite surfaces or sides 635A, 635B (where surfaces 635A, 635B are shown in the top view of FIG. 10I). Balloon 634 includes an inflation tube 636 positioned for placement at the underarm or elbow of the patient. In one embodiment, opposite surfaces 635A, 635B of balloon 634 are each configured in a generally flat planar shape and are parallel to each other. In this embodiment, balloon 634 may be flipped with the respect to the orientation shown in FIG. 10I to be used for the right or left arm of the patient. In another embodiment, opposite surfaces 635A, 635B of balloon 634 are each configured in a curved shape (e.g., where side 635A is convexly curves and side 635B is concavely curved) to wrap around right or left arm of the patient as shown in the top view of FIG. 10I. In this embodiment, balloon 634 may be configured as a balloon for use on the right arm or left arm depending on the placement of tube 636 with respect to balloon 634 as shown in the top view of FIG. 10I.

FIG. 10J illustrates balloon 638 shaped and configured for placement at a flank. In one embodiment, balloon 638 is configured in a generally rectangular shape having curved edges and opposite surfaces or sides 639A, 639B (where surfaces 639A, 639B are shown in the top view of FIG. 10J). Balloon 638 includes an inflation tube 640 positioned for placement at left or right lateral portion of the lower back of a patient. In one embodiment, opposite surfaces 639A, 639B of balloon 638 are each configured in a generally flat planar shape and are parallel to each other. In this embodiment, balloon 638 may be flipped with the respect to the orientation shown in FIG. 10J to be used for the right or left lateral portions of the lower back of the patient. In another embodiment, opposite surfaces 639A, 639B of balloon 638 are each configured in a curved shape (e.g., where side 639A is convexly curves and side 639B is concavely curved) to wrap around the flank of the left or right side of the lower back of the patient as shown in the top view of FIG. 10J. In this embodiment, balloon 638 may be configured as a balloon for use on the right side of the lower back or left side of the lower back as shown in the top view of FIG. 10J.

In accordance with a method of the disclosure, (i) a target region or area of tissue to be tightened, coagulated, contoured or sculpted is identified, (ii) a balloon having a shape configured to correspond to the shape of the target region or a portion thereof is selected, (iii) a small incision is made in an inconspicuous location adjacent the target region or area, (iv) the balloon, preferably mounted to an elongate introducer or probe, is inserted along a desired tissue plane in a folded condition through the incision into the target area, (v) the balloon is inflated to dissect tissue along the tissue plane to separate tissue along the plane, (vi) the plasma device is inserted (with or without removing the balloon prior to or during use of the plasma device) and activated to provide cool plasma to the tissue along the dissected plane to achieve the desired effect of tissue tightening, contouring, sculpting, and/or coagulating, and (vii) the plasma device is removed and the incision is closed.

Balloons also have the advantage that they tamponade tissue as they expand, so the techniques of the present disclosure reduce bleeding and when used with the plasma generators described above may result in faster recovery times for patients and better cosmesis.

It is to be appreciated that the various features shown and described are interchangeable, that is a feature shown in one embodiment may be incorporated into another embodiment. By way of example, one or more kits containing balloons configured and dimensioned for use in connection with treating specific target areas or regions (e.g., neck, abdomen, etc.) may be provided. A plasma delivery device may be included in a sterile package or enclosure with such balloon(s) as a kit for a specific procedure. In one embodiment, a surgical kit may include a sterile enclosure with a plasma generator and a balloon device for a specific procedure, where each item in the kit is sterilized before sealed herein. In another embodiment, the surgical kit may include a plasma generator and a plurality of balloon devices disposed in the sterile package or enclosure, where a user (e.g., a surgeon) selects the appropriately configured and dimensioned balloon as necessary. In addition, a system of the present disclosure includes one or more balloon dissection devices, one or more plasma delivery devices and a generator configured to provide gas and energy to the plasma delivery device.

It is further contemplated that the techniques described in the present disclosure may be used in conjunction with other procedures, such as liposuction and fat liquidation techniques. For example, during liposuction, a cannula is inserted into a tissue plane of interest and a vacuum or aspiration device attached to the cannula aspirates fat from the tissue plane via the cannula to remove the fat from the tissue plane. Liposuction techniques may be used in conjunction with fat liquidation techniques, such as, ultrasound-assisted liposuction (UAL), laser assisted liposuction (LAL), etc., which apply energy via sound or light to liquefy or break down fat cells in the tissue plane of interest to make the removal of fat via the cannula and/or vacuum easier and less invasive. Fat liquidation techniques may include injecting the tissue plane or target area with photo-absorbing nanoparticles, which are excited when light in predetermined wavelengths (e.g., near infrared) is applied to the tissue plane (e.g., via a laser or other light source) causing the fat in the tissue plane to melt or liquefy. The liquified fat is easily removed via aspiration. Exemplary fat liquidation techniques are described in U.S. Pat. Nos. 9,333,258; 9,333,259; 9,522,289 and 10,188,461, the contents of which are hereby incorporated by reference.

In one embodiment, a balloon device, such as any of devices 602, 606, 610, 614, 618, 622, 626, 630, 634, 638 described above, is inserted into a subcutaneous tissue plane or layer (e.g., through an incision) and inflated to dissect tissue to create a dissected tissue plane. Then, a liposuction procedure is performed to remove fat from the tissue plane. The liposuction procedure may include the fat liquidation techniques described above for easier fat removal. After the liposuction procedure is completed, a plasma device (as described above, for example, plasma generators 14, 100, 200, 300) is used to apply a plasma beam to the tissue plane and coagulate the tissue to achieve the desired effect.

In another embodiment, a liposuction procedure is performed first (i.e., before the insertion of a balloon device) to remove fat from a subcutaneous tissue plane or layer. The liposuction procedure may include the fat liquidation techniques described above for easier fat removal. Then, a balloon device, such as any of devices 602, 606, 610, 614, 618, 622, 626, 630, 634, 638 described above, is inserted into a subcutaneous tissue plane or layer (e.g., through an incision) and inflated to dissect tissue to create a dissected tissue plane. Then, a plasma device (as described above, for example, plasma generators 14, 100, 200, 300) is used to apply a plasma beam to the tissue plane and coagulate the tissue to achieve the desired effect.

In a further embodiment, a balloon device, such as any of devices 602, 606, 610, 614, 618, 622, 626, 630, 634, 638 described above, is inserted into a subcutaneous tissue plane or layer (e.g., through an incision) and inflated to dissect tissue to create a dissected tissue plane. Then, any one of the fat liquidation techniques described above may be used to liquefy the fat in the tissue plane. After the fat liquidation is completed, a plasma device (as described above, for example, plasma generators 14, 100, 200, 300) is used to apply a plasma beam to the tissue plane and coagulate the tissue to achieve the desired effect.

In yet another embodiment, any one of the fat liquidation techniques described above is performed first (e.g., via an incision through the patient tissue and before insertion of the balloon device). Then, a balloon device, such as any of devices 602, 606, 610, 614, 618, 622, 626, 630, 634, 638 described above, is inserted into a subcutaneous tissue plane or layer (e.g., through an incision) and inflated to dissect tissue to create a dissected tissue plane. Then, a plasma device (as described above, for example, plasma generators 14, 100, 200, 300) is used to apply a plasma beam to the tissue plane and coagulate the tissue to achieve the desired effect.

While the disclosure has been shown and described with reference to certain preferred embodiments thereof, it will be understood by those skilled in the art that various changes in form and detail may be made therein without departing from the spirit and scope of the disclosure as defined by the appended claims.

Furthermore, although the foregoing text sets forth a detailed description of numerous embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '______' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

What is claimed is:

1. A surgical method comprising:

creating an entry incision through a patient's skin;

aspirating fat from a subcutaneous tissue plane beneath the patients skin via the entry incision, the subcutaneous tissue plane including individual bands of a fibroseptal network;

applying helium-based plasma in the subcutaneous tissue plane, the helium-based plasma coagulates the individual bands and reduce laxity in the patient's skin, the helium-based plasma finds untreated bands of the individual bands that represents the path of least resistance for flow of RF energy in a plasma beam, the path of least resistance being a band having lower impedance relative to an adjacent band; and drawing the helium-based plasma through the subcutaneous tissue plane such that the path of least resistance constantly changes, in response to increasing tissue impedance of the treated individual bands, and the helium-based plasma alternates to at least one other band of the individual bands to effect 360 degree tissue treatment, wherein a current used to generate the helium-based plasma is selected such that, as impedance of the treated individual bands increases, the helium-based plasma alternates to an untreated individual band to limit heating of the treated bands.

2. The method of claim 1, wherein the applying the helium-based plasma includes:

flowing helium over an energized electrode to ionize a portion of the flowing helium to generate plasma for coagulating the tissue, wherein applying the helium-based plasma produces rapid tissue heating of the individual bands sufficient to cause collagen contraction followed by immediate cooling to minimize unintended thermal injury to adjacent tissue.

3. The method of claim 2, wherein less than 0.1% of the flowing helium is ionized to create the plasma and greater than about 99.9% of the flowing helium remains un-ionized, wherein the flow of un-ionized helium draws heat away from the coagulated tissue.

4. The method of claim 1, wherein the helium-based plasma is applied in a wanding motion to optimize distribution of the plasma.

5. The method of claim 1, wherein the helium-based plasma is applied at a constant power output level for a range of tissue impedances.

6. The method of claim 1, wherein the helium-based plasma is applied at a power output level of about 40 watts for tissue impedances on a range of about 125 ohms to at least about 5000 ohms.

7. The method of claim 1, wherein the aspirating fat includes at least one of an ultrasound-assisted liposuction technique, a laser assisted liposuction technique, and/or a power assisted liposuction technique.

8. The method of claim 1, further comprising liquifying the fat in the subcutaneous tissue plane before aspirating.

9. The method of claim 8, wherein the liquifying the fat includes:

injecting the subcutaneous tissue plane with photo-absorbing nanoparticles; and exciting the photo-absorbing nanoparticles with light of a predetermined wavelength.

10. A surgical method further comprising:

creating an entry incision through a patient's skin;

disposing a balloon device through the entry incision, the balloon device is disposed in a subcutaneous layer by a plasma generator;

inflating the balloon to dissect tissue to create the subcutaneous tissue plane;

aspirating fat via the entry incision; and applying helium-based plasma in the subcutaneous tissue plane to coagulate tissue and reduce laxity in the patient's skin.

11. The method of claim 10, wherein the balloon device is disposed in a subcutaneous layer by a tunneling member.

12. The method of claim 10, wherein the balloon is inflated with helium supplied by the plasma generator.

13. The method of claim 10, further comprising deflating the balloon device and removing the balloon device before the applying of the helium-based plasma.

14. The method of claim 10, wherein the balloon device remains inflated during the applying of the helium-based plasma to promote flow of the plasma to extremities of the subcutaneous tissue plane.

15. The method of claim 10, wherein the balloon device is configured to correspond to an area of skin of a patient to be tightened.

16. The method of claim 15, wherein the balloon device is configured to correspond to at least one of a patient's buttocks, abdomen, arms, legs, neck, forehead and/or chin.

17. A surgical method comprising:

creating an entry incision through a patient's skin;

disposing a balloon device through the entry incision;

inflating the balloon to dissect tissue to create a subcutaneous tissue plane, aspirating fat via the entry incision; and applying helium-based plasma in the subcutaneous tissue plane to coagulate tissue and reduce laxity in the patient's skin, wherein the balloon device remains inflated during the applying of the helium-based plasma to promote flow of the plasma to extremities of the subcutaneous tissue plane.

* * * * *